(12) United States Patent
Aerts

(10) Patent No.: US 7,632,654 B2
(45) Date of Patent: Dec. 15, 2009

(54) MEANS AND METHODS FOR DETECTING ENDOGLYCOSIDASE ACTIVITY

(75) Inventor: Johannes Maria Franciscus Gerardus Aerts, Abcoude (NL)

(73) Assignee: Academisch Ziekenhuis bij de Universiteit van Amsterdam, Amsterdam (NL)

( * ) Notice: Subject to any disclaimer, the term of this patent is extended or adjusted under 35 U.S.C. 154(b) by 66 days.

(21) Appl. No.: 10/977,509

(22) Filed: Oct. 29, 2004

(65) Prior Publication Data

US 2005/0158814 A1    Jul. 21, 2005

Related U.S. Application Data

(63) Continuation of application No. PCT/NL2003/00316, filed on Apr. 29, 2003.

(60) Provisional application No. 60/376,107, filed on Apr. 29, 2002.

(30) Foreign Application Priority Data

Apr. 29, 2002    (EP)    ................................ 02076854

(51) Int. Cl.
  *C12Q 1/34*    (2006.01)
  *C12N 9/24*    (2006.01)
(52) U.S. Cl. ........................................ 435/18; 435/200
(58) Field of Classification Search ........................ None
  See application file for complete search history.

(56) References Cited

U.S. PATENT DOCUMENTS

| 4,859,581 | A | * | 8/1989 | Nicolson et al. | ............... | 435/4 |
| 5,705,634 | A | * | 1/1998 | Bredehorst et al. | .......... | 536/124 |
| 5,767,364 | A | * | 6/1998 | de Silva et al. | ............. | 800/290 |
| 5,928,928 | A | * | 7/1999 | Aerts | ........................ | 435/201 |
| 6,057,142 | A | * | 5/2000 | Aerts | ........................ | 435/209 |
| 6,200,951 | B1 | * | 3/2001 | Gray et al. | .................... | 514/2 |
| 6,221,591 | B1 | * | 4/2001 | Aerts | ........................... | 435/6 |

(Continued)

FOREIGN PATENT DOCUMENTS

WO    WO 03/093497 A1    11/2003

OTHER PUBLICATIONS

Suganuma T, et al. (1997)Study of the action of human salivary alpha-amylase on 2-chloro-4-nitrophenyl alpha-maltotrioside in the presence of potassium thiocyanate. Carbohydrate Res vol. 303: pp. 219-227.*

(Continued)

*Primary Examiner*—Anand U Desai
*Assistant Examiner*—William W Moore
(74) *Attorney, Agent, or Firm*—TraskBritt

(57) ABSTRACT

The invention discloses a method for detecting an activity of an endoglycosidase. The method includes providing the endoglycosidase with a substrate of the endoglycosidase and detecting cleavage of the substrate. The method further includes at least partly inhibiting the transglycosidase activity of the endoglycosidase. The transglycosidase activity may be inhibited by chemically modifying the substrate such that transglycosylation of the substrate by the endoglycosidase is at least partly inhibited while the endoglycosidase is still capable of cleaving the substrate. In one embodiment, the substrate comprises an oligosaccharide chain. Compounds and kits suitable for use in a method of the invention are also disclosed. Methods involving competitive inhibitors are also disclosed as are methods for the synthesis of glycosylated substrates involving the transglycosidase activity of an endoglycosidase.

15 Claims, 16 Drawing Sheets

U.S. PATENT DOCUMENTS

| | | | | |
|---|---|---|---|---|
| 6,303,118 | B1* | 10/2001 | Aerts | 424/94.61 |
| 6,372,212 | B1* | 4/2002 | Gray | 424/94.61 |
| 6,399,571 | B1* | 6/2002 | Gray et al. | 514/12 |
| 6,844,179 | B1* | 1/2005 | Nakanishi et al. | 435/201 |
| 6,896,884 | B2* | 5/2005 | Aerts | 424/94.61 |
| 7,098,324 | B2* | 8/2006 | Haigler et al. | 536/24.1 |
| 2003/0017570 | A1* | 1/2003 | Gray | 435/196 |
| 2003/0087414 | A1* | 5/2003 | Aerts et al. | 435/226 |

OTHER PUBLICATIONS

Kanie O, et al (1993) Acceptor-substrate recognition by N-acetylglucosaminyltransferase-V: Critical role of the 4 . . . Carbohydrate Res vol. 243: pp. 139-164.*

Winn-Deen ES, et al (1988) Development of a direct assay for alpha-amylase. Clin Chem vol. 34: pp. 2005-2008.*

Rechter M, et al (1999) A cellulose-binding domain-fused recombinant human T cell connective tissue-activating peptide-III mainfests heparanase activity. BBRC vol. 255: pp. 657-662.*

Brown TL et al (1981) Detection of alpha amylase activity in unprocessed preamylase produced in the cell-free translation of porcine pancreatic RNA. J Biol Chem, vol. 256, No. 21, pp. 10743-10746.*

Weissman B. et al., 1954, Journal of Biological Chemistry, vol. 208, No. 1, pp. 417-429.*

MacLachlan, G., et al., 1994, "Endo-1, 4-.beta.-Glucanase, Xyloglucanase, and Xyloglucan Endo-Transglycosylase Activities Versus Potential Substrates in Ripening Tomatoes", Plant Physiology, vol. 105, No. 3, pp. 965-974.*

De Silva, J. et al., 1993, "Molecular Characterization of a Xyloglucan-Specific Endo-(1-4)-.beta.-.sub.D -Glucanase (Xyloglucan Endo-Transglycosylase) From Nasturitium Seeds", The Plant Journal, vol. 3, No. 5 pp. 701-711.*

Fujita, M., et al., 2001, "A novel disaccharide substrate having 1,2-oxazoline moiety for detection of transglycosylating activity of endoglycosidases", Biochimica et Biophysica Acta, vol. 1528, No. 1, pp. 9-14.*

Usui, T., et al., 1990, "Enzymic synthesis of useful chito-oligosaccharides utilizing transglycosylation by chitinolytic enzymes in a buffer containing ammonium sulfate", Carbohydrate Research, vol. 203, No. 1, pp. 65-77.*

Collinge, et al., 1993, "Plant Chitinases", Plant Journal, vol. 3, No. 1, pp. 31-40.*

PCT International Search Report, PCT/NL03/00316 dated Aug. 29, 2003.

Araiki et al., "Structure of a Triphosphonopentaosylceramide Containing 4-O-Methyl-N-acetylglucosamine from the Skin of the Sea Hare, *Aplysia kurodai*," The Journal of Biological Chemistry, Oct. 15, 1987, pp. 14141-14145, vol. 262, No. 29.

Bardales et al., "Transglycosylation and Transfer Reaction Activities of Endo-alpha-N-acetyl-D-galactosaminidase from *Diplococcus (Streptococcus) pneumoniae*," The Journal of Biological Chemistry, Nov. 25, 1989, pp. 19893-19897, vol. 264, No. 33.

Hollack et al., "Marked Elevation of Plasma Chitotriosidase Activity," Journal of Clinical Investigation, Mar. 1994, pp. 1288-1292, vol. 93.

Abstract of Japanese Patent 03 157391, filed Nov. 15, 1989, published Jul. 5, 1991.

Park et al., Structure, specificity and function of cyclomaltodextrinase, a multispecific enzyme of the alpha-amylase family, Biochimica et Biophysica Acta, 2000, pp. 165-185, vol. 1478.

* cited by examiner

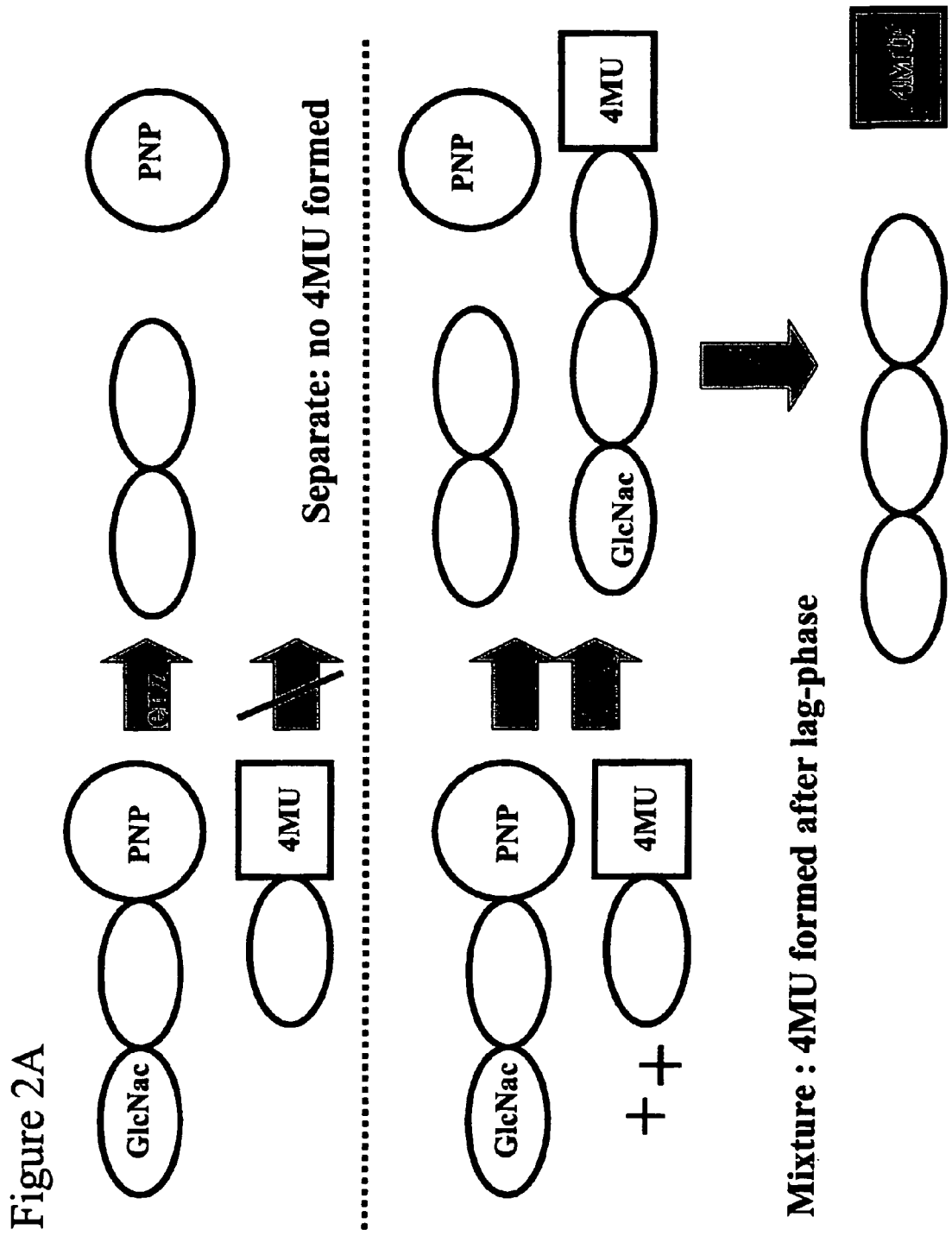

CHIS-1: *(4-deoxy-GlcNAc)-GlcNAc-UMB*

Figure 7  Response to therapeutic interventions

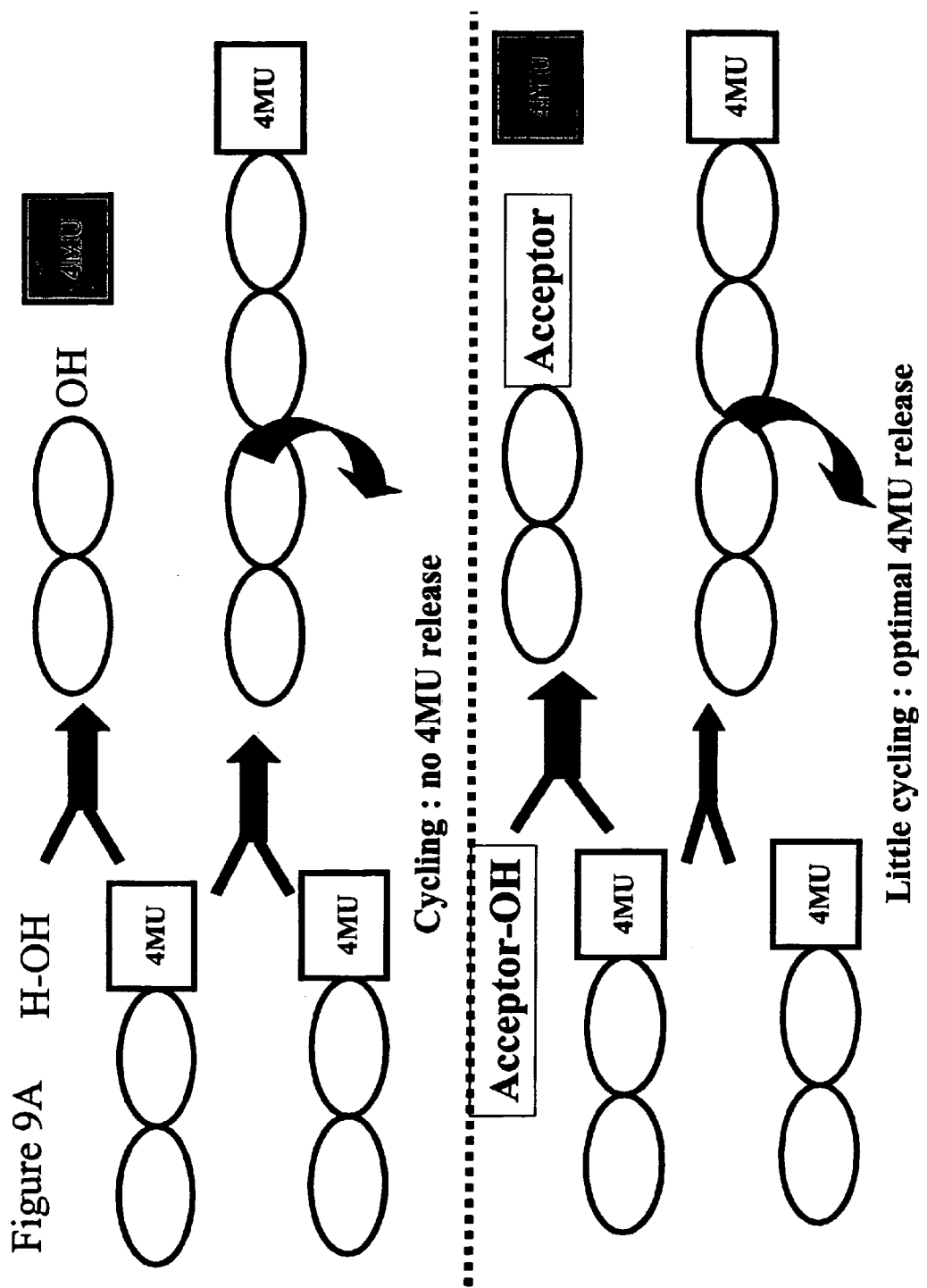

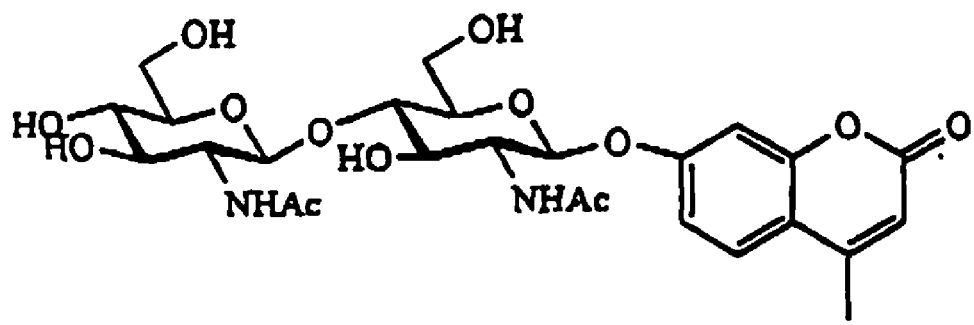
GlcNAc-β-(1, 4)-GlcNAc-β-UMB
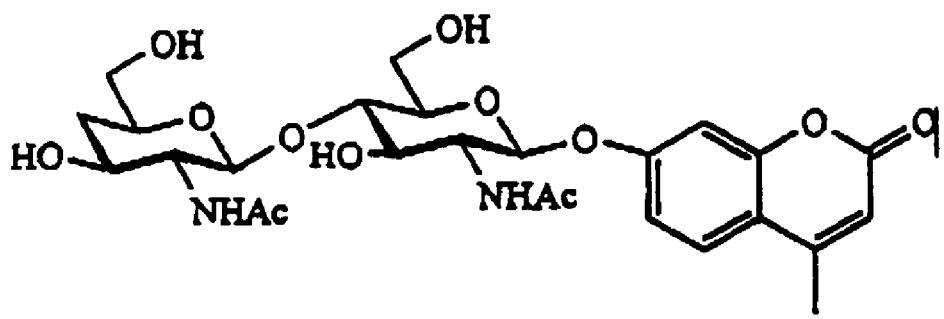
(4-deoxy-GlcNAc)-β-(1, 4)-GlcNAc-β-UMB
Structures of GlcNAc-β-(1, 4)-GlcNAc-β-ѰMB and
(4-deoxy-GlcNAc)-β-(1, 4)-GlcNAc-β-UMB
Figure 11

MEANS AND METHODS FOR DETECTING ENDOGLYCOSIDASE ACTIVITY

CROSS-REFERENCE TO RELATED APPLICATIONS

This application is a continuation of PCT/NL03/00316 filed Apr. 29, 2003, designating the United States of America, corresponding to PCT International Publication WO 03/093497 (published in English on Nov. 13, 2003), the contents of which are incorporated herein in its entirety. PCT/NL03/00316 itself claims priority to EP 02076854.5, filed Apr. 29, 2002, and US 60/376,107, filed Apr. 29, 2002.

TECHNICAL FIELD

The invention relates to diagnostics. More specifically the invention relates to detection of endoglycosidase activity and diagnostics of infertility and diseases wherein an altered amount of an endoglycosidase is involved.

BACKGROUND

Glycopolymers are major components of the extracellular matrix of organisms. These matrixes can be remodeled and/or degraded by endoglycosidases and exoglycosidases. Examples of endoglycosidases are chitinase, lysozyme, heparanase, hyaluronidase, and cellulase. Chitinase.

Chitin is the linear polymer of beta 1-4 linked N-acetylglucosamine residues. It is the second most abundant glycopolymer on earth that is present in cell walls and coatings of a very large variety of organisms. Chitin is degraded in a stepwise manner by the concerted action of endoglycosaminidases (chitinases) and exoglucosaminases. The chitinases are widely distributed in nature and are known to fulfill several critical biological functions. Examples are roles in food processing, remodeling and defense against chitin-containing pathogens. Chitinases can be also industrially employed, for example in crop protection, food preservation, bio-degradation of chitin-containing waste product and production of chito-oligomers or other fine chemicals. A novel area of application is in the field of diagnosis and monitoring of specific human disease conditions as well as the assessment of chitinase deficiency as potential risk factor for specific infections.

The existence of endogenous chitinases in man has only recently been unequivocally demonstrated (Hollak et al., 1994). The enzyme was initially discovered in patients with Gaucher disease, an inherited lysosomal storage disorder that is caused by a deficiency in the lysosomal enzyme glucocerebrosidase. The level of chitinase activity is generally 1000-fold increased in plasma of symptomatic Gaucher patients. The corresponding enzyme, characterized in great detail at the level of protein, RNA and gene, has been named chitotriosidase. The features of the enzyme have been described in a series of publications (Renkema et al., 1995; Boot et al., 1995; Renkema et al., 1997; Renkema et al., 1998; Boot et al., 1998; Boot et al., 2001). It was shown by us that in tissues of Gaucher patients, macrophages transform to lipid-laden pathological cells that synthesize and secrete large quantities of chitotriosidase. The concomitant marked elevation of enzyme in plasma reflects the presence of abnormal macrophages in tissues and is currently used for the diagnosis, the detection of onset and progression of disease and the monitoring of efficacy of therapeutic intervention (Aerts et al., 1997; Cox et al., 2000; Casal et al., 2002, Giraldo et al., 2002). Deficiency in the enzyme is a frequent trait and is predominantly caused by a 24 bp duplication in the chitotriosidase gene (locus 1q31). In various ethnic groups the frequency of carriers for this mutation is about 35%. A convenient test for establishing an individual's chitotriosidase genotype has been developed (Boot et al., 1998; Choi et al., 2001).

Chitotriosidase is the true analogue of chitinases from lower organisms. It can efficiently degrade chitin, releasing chitotriose and chitobiose fragments from the reducing end of the polymer. Recently, a human mucinase was discovered which also displays chitinase activity (Boot et al., 2001). The enzyme shows an extreme acid stability and acid pH optimum for activity. This enzyme has been named acidic mammalian chitinase (AMCase). It is not present in serum in contrast to chitotriosidase.

It has been earlier conceived that expression of chitinase activity is a very specific phenomenon that is uniquely related to chronic activation of tissue macrophages. This novel thought might be exploited for various diagnostic purposes and could also revolutionize non-invasive monitoring of progression of diseases and correction by therapies. Proof of concept has indeed been obtained: chitotriosidase has been found to be expressed by chronically activated macrophages in several pathological conditions resulting in elevated enzyme activity levels in bodily fluids such as plasma, cerebral spine fluid or urine. Examples of conditions showing such type of abnormalities are several lysosomal lipid storage disorders (Guo et al., 1995) sarcoidosis and visceral Leishmaniasis (Hollak et al, 1994), thalassemia (Barone et al., 2001), arteriosclerosis (Boot et al, 1999), HES (hydroxyethylstarch)-induced prunitis, CGD (chronic granulomatosis disease), Crohn's disease, Tangier disease, and arteriosclerosis (Aerts and coworkers, not yet published observations).

Detection and quantitation of chitotriosidase protein in plasma with immunological techniques is problematic. In healthy subjects the protein concentration is on average only 5 ng/ml of serum.

The fact that the protein can catalyse a specific reaction allows in principle a more sensitive and quantitative detection by measuring this enzymatic activity. Unfortunately, again several limitations exist in this connection. Chitin degradation is generally followed using colloidal chitin as substrate and the indirect detection of released fragments. The latter is accomplished by hydrolysis of fragments upon incubation with hexosaminidase, whereafter free N-acetylglucosamine moieties are detected. This method is very insensitive and not directly proportional to the initial chitinase activity. Assays using as substrate radiolabeled chitin or chitins conjugated with chromophores have also a very poor sensitivity and do not render reliable results with plasma samples. A several hundred-fold more sensitive assay has been earlier described by us (Hollak et al.,1994). The assay is based on the use of 4-methylumbelliferyl-chitotrioside as substrate. Alternatively, 4-MU-chitobiose or 4-MU-chitotetraose can be used as substrate (Hollak et al., 1994). Chitotriosidase is able to cleave these synthetic substrates, thus releasing the fluorescent 4-methylumbelliferone. The assay with the above mentioned 4-MU-substrates has a major drawback. No use can be made of saturating substrate concentrations due to apparent substrate inhibition (see for example FIG. 1). Consequently, the assay has to be performed at sub-saturating substrate concentration. As inevitable result of this, the measured enzymatic activity is intrinsically not strictly related to the input of enzyme and only linear in time for a very short period. The results of assays with plasma samples can only be well interpreted if additionally parallel assays are run with standard (pure) chitotriosidase preparations and assay time and input of plasma protein are extensively varied. Considerable expertise is required to obtain reproducible results with this method. In conclusion, at present no convenient and widely applicable method is available that allows very sensitive and quantitative detection of chitotriosidase and comparable chitinases.

Lysozyme.

Lysozyme catalyzes the hydrolysis of certain mucopolysaccharides of bacterial cell walls. Specifically, it catalyzes the hydrolysis of the bacterial cell wall beta(1-4) glycosidic linkages between N-acetylmuramic acid and N-acetyiglucosamine, but not the glycosidic bond between N-acetylglucosamine and N-acetylmuramic acid. Lysozyme is involved in bacteriolytic defensive and immune response. It is present in organs and bodily fluids of the human, including plasma, where it is found in monocytes and macrophages, neutrophils and g~andular cells. Serum lysozyme is a potential marker for activity of monocytes and macrophages. The serum level of lysozyme is for instance elevated in patients with an infection, autoimmune disease and/or cancer. Examples of bacterial and viral infections are tuberculosis, pneumonia, meningitis, otitis media, urinary tract infections, sepsis and acquired immunodeficiency syndrome. Examples of autoimmune diseases are rheumatic disorders as e.g. rheumatoid arthritis, Inflammatory Bowel Disease, as e.g. Ulcerative Colitis and Crohn's disease, chronic respiratory inflammatory diseases as e.g. chronic bronchitis and chronic sinusitis, interstitial pulmonary diseases as sarcoidosis, and diabetes. Examples of cancer are colorectal cancer, leukemia as e.g. Hodgkin's disease and lung carcinoma.

For measurement of the activity of lysozyme several assays are available. Lysozyme is most frequently analyzed by a variety of methods using Micrococcus lysodeikticus cells as substrate, such as the turbidimetric assay. Some improvement in the turbidimetric method was obtained by Morsky (1983). This modified lysozyme assay has improved routine clinical use in regard to analysis speed, sensitivity, linearity and reproducibility. The reaction course of bacterial cell wall lysis for quantifying lysozyme in serum and urine can also be applied to the solid phase with agarose gel as reaction medium: the lysoplate method (Maeda et al., 1980). The reproducibility of this method is reasonable but labour intensive. Furthermore the results are not always reproducible due to biological factors in the sample or agar batch.

In contrast to the turbidimetric method, the enzyme-linked immunosorbent assay (ELISA) (Taylor et al., 1992), the double-antibody radioimmunoassay (Thorsteindottir et al., 1999) and the electroimmunodiffusion technique measure the concentration of lysozyme. Comparison of lysozyme values obtained with the ELISA and turbidimetric methods showed good correlation. The major drawback in both the ELISA, radioimmunoassay and electroimmunodiffision assay is still the fact that neither of these immunological techniques measures the activity of lysozyme. Their use is also limited by their degree of sensitivity and the presence of lysozyme isozymes. Another drawback concerning lysozyme assays is the lack of uniformity in standardization of lysozyme assays. Thus, the results are not always unambiguously interchangeable, and clinical reference values differ greatly. In conclusion, a simple, rapid, sensitive and specific assay to measure the lysozyme activity is not available.

Hyaluronidase

Hyaluronan, hyaluronic acid (HA), is one of the principal glycosaminoglycans of the extracellular matrix. It consists of a high molecular weight polymer of repeating units of N-acetylglucosamine and D-glucuronic acid. It is believed to have numerous important biologic functions, including modulation of cell proliferation, migration and differentiation and is believed to be crucial in tissue remodeling, e.g. during embryogenesis and wound healing, in tumorigenesis, angiogenesis and inflammation.

Clinically, aberrations of HA metabolism are associated with processes such as adult respiratory distress syndrome, organ transplant oedema and rejection, and as a marker for cancer remission and relapse. The binding of exogenous FIA to cell surface receptors, the most important one being CD44, mediates endocytosis of extracellular HA, leading to its degradation by lysosomal hyaluronidase. Hyaluronidase is the enzyme that degrades HA. This endoglycosidase cleaves the N-acetyl-(1-*4)-glucosaminic bonds in HA, forming even-numbered oligosaccharides, with mainly tetrasaccharides as the smallest fragments (Menzel et al., 1998); digestion with testicular hyaluronidase results in the exclusive cleavage of the N-acetylhexosaminidic linkages, the products comprising a series of oligosaccharides with N-acetylglucosamine at the reducing terminus. Upon exhaustive digestion, the tetrasaccharide is the major product, closely followed by the hexasaccharide and smaller amounts of higher oligosaccharides, while only a small proportion of disaccharide is found in a digest of this type.

Hyaluronidases from vertebrate tissues can be separated into two classes that have very different biological functions. The major hyaluronidase in human plasma is the hyaluronoglucosamindase-1. This enzyme is expressed in multiple tissues. In the sperm plasma membrane and acrosomal membrane an enzyme with hyaluronidase activity is present, the sperm adhesion molecule 1 gene or PH-20. To penetrate the cumulus layer, a hyaluronan-rich extracellular matrix surrounding the oocyte, the sperm uses this enzyme to break down the hyaluronan. This enzyme is a marker for the sperm function.

Hyaluronan (HA) and hyaluronidase (HAase) are involved in malignant transformation and cancer progression. In many malignancies, levels of HA correlate with metastatic behaviour while HAase suppress malignant progression. In bladder cancer, hyaluronic acid and hyaluronidase are used as biological markers for bladder tumour, angiogenesis and metastasis, being secreted in urine. An elevated urinary HA indicates the diagnosis of bladder cancer regardless of tumour grade and the urinary HAase levels correlates with the malignant potential of bladder cancer, being grade 2 and grade 3 (Lokeshwar et al., 2000). The hyaluronic acid and hyaluronidase (HA-HAase) test is the only non-invasive assay described that detects HA and HAase, because it measures in urine. Other HA and HAase measuring tests use sera as biological samples. The HA-HAase test for urine is an ELISA-like assay using e.g. an avidin-biotin-peroxidase color detection system. This test has 90-92% sensitivity and 80-84% specificity for bladder cancer (and is currently evaluated in multicenter trial settings (Lokeshwar, 2001).

Despite the sensitivity and specificity of the HA-HAase test, in current practice cystoscopy is the gold standard for detecting bladder cancer and evaluating tumor recurrence, while voided urine or bladder wash cytology is often used as an adjunct to cystoscopy for detecting high-grade bladder cancer. The voided urine cytology is the standard non-invasive tumor specific marker and evaluates malignancy based on cellular morphology. Voided urine cytology has an excellent specificity but a poor sensitivity (Brown 2000). However, it is not sensitive for detecting low-grade disease. Also variability among those interpreting cytology findings is significant. Moreover, urine cytology is not quantitative. In conclusion, urine cytology in its present form cannot replace cystoscopy as a method for detecting and monitoring bladder cancer, but should be used as an additional application. An ideal non-invasive test should be sensitive, specific, rapid, technically simple and have low intra-assay and interassay variability.

The most commonly used hyaluronidase assays, which are either insensitive or lack specificity, are based upon the measurement of the generation of new reducing N-acetylamino groups, or loss of viscosity or turbidity. Other assays are dye binding assays, zymogram electrophoretic technique or enzyme activity measurement based on the Morgan-Elson reaction. All these assays are relatively cumbersome and insensitive. For large-scale measurements application of the modern ELISA-like microtiter assay by Frost and Stem (1997) may be more convenient. This study describes a sensitive, rapid microtiter-based assay for hyaluronidase activity that does not require highly specialized biological reagents. However, this assay is not accurate, time- and dose-dependent. Hyaluronidase activity can also be measured in venoms using capillary electrophoresis or by USP XXII assay but also these assays are not sensitive as described by Pattanaargson et al., 1996.

Heparanase.

Heparan sulfate (HS) and heparan sulfate proteoglycans (HSPGs) are acidic complex polysaccharides found on the cell surface, in the extracellular matrix and vascular basal lamina. These biopolymers play an important role in cell proliferation, differentiation, migration and shape. The HS chains are originally synthesized as a polysaccharide of alternating N-acetyl-glucosamine (GlcNAc) and glucuronic acid (GlcUAu) that are enzymatically modified to a complex polysaccharide containing sulphate rich and sulphate poor regions. The enzyme heparanase (Hpa) cleaves the heparan sulfate glycosaminoglycans from the proteoglycan core proteins and degrade them to small oligosaccharides. Heparanase is an endoglucuronidase, cleaving the linkage between glucuronic acid (GlcUA) and N-acetyl-glucosamine (GlcNAc). Hpa I, the dominant heparanase in mammalians, is a hydrolase cleaving the HS chains at specific places and not an eliminase as heparinase from Flavobacterium heparinuin. Heparanase is expressed in a wide variety of tissues and cells. (Barne, 2001 and Parish et al, 2001). It plays a major role in early embryogenesis, morphogenesis, pregnancy and development to inflammation, wound healing, and tumor angiogenesis and metastasis. Human platelets have been shown to contain high levels of heparanase activity, capable of degrading endothelial cell surface, tumour-derived and ECM derived HSPG as well as free HS chains and heparin. Heparanase is able to facilitate cell invasion by degrading the extracellular matrix and the vascular basement, needed for invasion of cancer in the metastatic phase and neovascularization. (See for review Parish et al, 1998 and Vlodavsky et al, 2001). The metastatic potential of tumour cells is related to their increased heparanase content. A heparanase assay is a diagnostic tool for cancer staging, since it has been suggested that heparanase plays a prominent role in cancer-associated processes. Indeed, it has been found that cancer patients had twice the serum heparanase levels as normal healthy adults.

It has been shown that HpaI can cleave the antithrombin-binding site in heparin, low molecular weight heparin (LMWH) and synthetic pentasaccharides containing an intact antithrombin III binding site, thereby inhibiting the anticoagulation function of these drugs that are given therapeutically or prophylaxis to patients with an increased risk for thrombosis. Heparin, LMWH and synthetic pentasaccharides are indicated as therapeutical in the acute phase of deep venous thrombosis or pulmonary embolism treatment and as prophylaxis for e.g. general surgery, acute myocardial infarction, ischemic stroke, intensive care patients and bedridden patients with a risk factor.

During therapy of patients with heparin, LMWH or pentasaccharides it is essential to monitor the activated clotting time to guide the heparin therapy during cardiac surgery, cardiac catherication and coronary interventions. The available clotting assays to measure the coagulation status of patients in heparin therapy are sensitive to the presence of small traces of heparin and tissue factor pathway inhibitor (Bladbj erg et al., 2000) and the presence of the endogenous heparanase in plasma. A simple heparanase/heparinase assay would be medical useful to monitor the therapy of the patients with heparin, LWMHs or synthetic polysaccharides and scientific useful to elucidate the pathways.

It has been shown that synthetic heparin mimicking compounds can inhibit heparanase and decrease the incidence of metastases. The role of heparanase in cancer and angiogenesis has not been elucidated, although the heparanase activity has been known for several decades. A major reason for the lack of studies of heparanase activity and heparanase inhibition has been due to the absence of a simple, rapid and sensitive assay for heparanase activity (Parish et al., 1999). Also for monitoring the heparanase activity in cancer and during therapy of patients with anticoagulants a reliable assay is necessary. In addition, a simple assay to measure heparanase activity would also be helpful in studying the activity of homologous proteins as e.g. the mammalian gene Heparanase 2 (McKenzie et al., 2000).

Different kinds of assays have been described for measuring heparanase activity. In one type of assay heparanase activity is detected by separating cleaved from uncleaved radioactivity labelled and fluorescence labelled HS using electrophoresis. In another type of assay heparanase activity is detected by incubating the sample in the presence of a solid phase support having immobilized thereon a substrate for the heparanase and separating cleaved from uncleaved substrate. Freeman et al. (2001) describe an example for this type of assay using histidine-rich glycoprotein as heparan sulphate binding protein. Another example is the assay described by Brenchley (2000), wherein two solid phase supports are used, one to bind the uncleaved and one to bind the cleaved HS. These assays are laborious. A simple, rapid, sensitive and specific assay to measure the heparanase activity is not available.

Cellulase.

Cellulose, the most abundant carbohydrate produced by plants, is an unbranched (1-4)-~-D-glucose polymer with repeating unit of cellobiose (glucose dimer) instead of glucose. Although cellulose is a simple polymer, it forms insoluble, crystalline microfibrils, but it also contains regions with less structure, the so-called amorphous zones. All organisms known to degrade cellulose efficiently produce a battery of enzymes with different specialties, which act together in synergism. This enzymatic hydrolytic system consists of three different enzymes and so catalytic reactions: (i) endoglucanases (EC), which can randomly hydrolyse the 1,4-~-glycosidyl linkages within the water-insoluble cellulose chains; (ii) exoglucanase or cellobiohydrolases (CBHs), which hydrolyse the 1,4-~-glycosidyl linkages of either the reducing or non-reducing ends of cellulose chains to form cellobiose and (iii) ~3-glucosidases or cellobiose, which converts the water soluble cellobiose into two glucose residues. Microorganisms, especially fungi, produce often mixtures of these enzymes. Together, these enzymes form a cellulolytic system and hydrolyse insoluble cellulose, both crystalline and amorphous, in a very efficient and synergistic way.

Several applications of cellulases are being developed for textile, food, and paper pulp processing (Beguin et al, 1994). Today, cellulase enzymes are used in different segments of the cotton textile industry. For the characterization of the cellulase in these contexts and for the insight in the complex mechanisms of hydrolysis, a rapid, sensitive test is desired.

Glucanase.

Beta-Glucans with 1,3-~3-glycosidyl linkages are present in a variety of organisms. Various beta 1,3 glucanases that cleave 1,3-~3-glycosidyl linkages have been described in lower organisms and plants. The cell wall of various pathogenic organisms contains beta 1,3-glucan and this structure exerts a potent effect on the immune system in man. Nothing is so far known about the catabolism of beta 1,3 glucan in man. Accurate detection of beta 1,3-glucanase activity is therefore highly desired.

Thus, endoglucanases are involved in a wide range of important (patho)biological processes. The concentration of such enzymes is often altered during a disease and during the process of counteracting/curing of a disease. Hence, the concentration of a certain endoglucanase is often indicative for the status of an individual. Detection of the concentration of such enzymes provides important information about a disease and/or the treatment of a disease. However, in spite of different tests developed in the art, detection of these enzymes is still cumbersome. The aim of the present invention is to provide improved, sensible and simple methods for detecting an activity of an endoglycosidase.

SUMMARY OF THE INVENTION

The invention provides a method for detecting an activity of an endoglycosidase comprising providing the endoglycosidase with a substrate of the endoglycosidase and detecting cleavage of the substrate, further comprising at least partly inhibiting the transglycosidase activity of the endoglycosidase. The invention enables improved tests for detecting activities of endoglycosidases which are involved in a wide range of important (patho) biological processes, such as lysosomal storage disease, chronic inflammation, sepsis, thalassemia, and bladder cancer.

Surprisingly, according to the teaching of the present invention test results can easily be improved by inhibiting the transglycosidase activity of the endoglycosidase. Apparently, transglycosidase activity is an important cause of unreliable test results of current tests. For instance, the phenomenon of substrate inhibition can be simply avoided by inhibiting transglycosidase activity of an endoglycosidase. If the transglycosidase activity is at least partly inhibited, a simple and reliable test for determining the activity of an endoglycosidase can be obtained. This is for instance shown in the examples for chitotriosidase. However, a method of the invention can be used for the detection of any other endoglycosidase, such as a mucinase, lysozyme, heparanase, hyaluronidase, cellulase and or glucanase.

In the examples it is shown that chitotriosidase is not only capable of cleaving chito-oligomers but can also donate the cleaved sugar moiety back to a cleaved substrate. In other words, chitotriosidase shows transglycosylase activity. This realization explains among other things the observed apparent substrate inhibition with chito-oligomers that is found to be strictly dependent on the absolute concentration of reducing end N-acetylglucosamine residues in the chito-oligomers. Increasing the substrate concentration implies increasing the chance that substrate molecules are used instead of water molecules as acceptor. For example, when 4-MU-chitobiose is used as substrate 4-MU-chitotetraose is preferentially formed at increasing substrate concentrations. The 4 MU-chitotetraose is next cleaved to 4-MU-chitobiose and the released chitobiose-unit will be added again preferentially to another 4MU-chitobiose molecule. This causes a continuous transfer of chitobiose units between substrate molecules without release of the fluorescent 4-MU. To the experimenter it appears that the enzyme is inhibited at these conditions, (see also FIG. 2B).

According to the present invention, a reliable and easy test for the detection of an activity of an endoglycosidase can be performed with a method of the invention wherein transglycosidase activity of the endoglycosidase is at least partly inhibited.

By an endoglycosidase is meant an enzyme, or a functional part, derivative and/or analogue thereof, capable of significantly cleaving sugar moieties from a substrate comprising an oligosaccharide.

By transglycosidase activity of an endoglycosidase is meant a capacity of the endoglycosidase to donate at least one sugar moiety to a substrate which is cleaved, and/or capable of being cleaved, by the endoglycosidase.

A functional part of a protein is defined as a part which has the same kind of properties in kind, not necessarily in amount. A functional derivative of a protein is defined as a protein which has been altered such that the properties of the protein are essentially the same in kind, not necessarily in amount. A derivative can be provided in many ways, for instance through conservative amino acid substitution.

A person skilled in the art is well able to generate analogous compounds of a protein. This can for instance be done through screening of a peptide library. Such an analogue has essentially the same properties of the protein in kind, not necessarily in amount.

In one embodiment of the invention the transglycosidase activity is inhibited by chemically modifying the substrate such that transglycosylation of the substrate by the endoglycosidase is at least partly inhibited while the endoglycosidase is still capable of cleaving the substrate. Preferably, the substrate comprises an oligosaccharide chain.

Transglycosylation of a substrate can be decreased by removing a hydroxyl group in a non-reducing end sugar moiety. In terms of the invention, removing a hydroxyl group means that the hydroxyl group is not present anymore, or that the hydroxyl group is still present but no longer available for binding of a sugar moiety. This can for instance be performed with a protection group, such as methoxy group.

Preferably, a hydroxyl group at the C4 position of sugar residues in the non-reducing end sugar moiety is removed, because a sugar moiety is usually bound at the C4 site. The hydroxyl group can be removed by substitution of the hydroxyl group by another group. Methods for chemical substitution reactions are well known by the skilled person and need no further explanation here. Preferably, the other group is a small group, such that the capability of the substrate of being cleaved by the endoglycosidase is retained. A large group often diminishes the capability, for instance because the substrate does not fit the enzymatic groove anymore. A large group also improves the chance of sterical hindrance.

A small group which is suitable for instance comprises a hydrogen atom or a methoxy group. Hence, in one embodiment a method of the invention is provided wherein the hydroxyl group is substituted by a hydrogen atom or a methoxy group. In yet another embodiment, transglycosylation of the substrate is decreased by substituting a carbon atom in a non-reducing end sugar moiety and a hydroxyl group bound to the carbon atom by an SH group.

Preferably, the carbon atom comprises a carbon atom at the C4 position in the non-reducing end sugar moiety. Preferably this carbon is at the C4 position, resulting in an SH group being bound to the carbon atom at the C4 position. In a preferred embodiment a method of the invention is provided wherein the sugar moiety comprises N-acetylglucosamine.

In a particularly preferred embodiment the so-called stopper group comprises a deoxy-group.

Transglycosylation of a substrate can also be counteracted by adding a molecule which is capable of transglycosylated by an endoglycosidase. If the molecule, also called an acceptor, is present in a higher concentration than the substrate, the chance is increased that an endoglycosidase donates a sugar moiety to the molecule instead of to the substrate. This effect is also established if only the local concentration of the molecule is higher, even though the overall concentration may be the same or even smaller than the substrate. By local concentration is meant herein the concentration in close vicinity of the enzyme. The local concentration of the molecule can be increased by a group, such as a lipid chain, which tends to be in the vicinity of the enzyme. Preferably, the molecule does not comprise water.

In a preferred embodiment, the molecule comprises a hydroxyl group that can act as an acceptor for transglycosylation. The molecule for example preferably comprises an alternative oligosaccharide. In terms of the invention, an alternative oligosaccharide means an oligosaccharide which is not exactly the same as the substrate.

One embodiment of the invention therefore provides a method of the invention, wherein the transglycosylation of the substrate is decreased by administration of a molecule capable of being transglycosylated by the endoglycosidase. Preferable the molecule comprises an alternative oligosaccharide.

According to the present invention, serum comprises an acceptor of the invention. The acceptor can be administrated in a pure form. Alternatively, the acceptor can be administered by adding an aliquot of serum comprising, the acceptor. In one aspect the invention therefore comprises a method wherein the molecule is derived from serum. In a further embodiment the invention provides a method of the invention wherein the substrate comprises an oligosaccharide and a leaving group. Preferably the oligosaccharide comprises 2-5 sugar moieties. Within this range there are endoglycosidases having a preference for, or higher specific activity, when provided with substrate having 2 sugar moieties, whereas other endoglycosidases have a preference for, or higher specific activity, when provided with somewhat longer sugar chains within the mentioned range of 2-5. Thus, within the range of 2-5 sugar moieties, the actual number of sugar moieties is preferably adapted to the preference for, or the specific activity of the particular endoglycosidase to be detected or quantified. For instance a heparanase typically has a preference for substrates having 3 sugar moieties in an oligosaccharide chain. On the other hand the number of sugar moieties in the oligosaccharide chain should also be balanced with the tendency of the enzyme to cut within the oligosaccharide. This latter process is, for optimal performance of the assay, preferably avoided by staying on the lower end of the range of 2-5.

The leaving group preferably comprises a group which can only be detected after it is cleaved from the substrate, facilitating on-line registration of an enzymatic reaction. Preferably, the leaving group is only fluorescent after it is cleaved. Alternatively, the group can always be fluorescent. In that case it is suitable to separate released leaving group moieties from (cleaved) substrate molecules. Detecting the intensity of fluorescence in the fraction containing the released leaving group moieties is indicative for the amount of cleaved substrate and, hence, for enzymatic activity.

In one embodiment of the invention, the leaving group comprises methyl-umbelliferyl, para-nitrophenyl, fluorescein and/or a functional part, derivative and/or analogue thereof.

Biological materials can contain various enzymes with overlapping substrate specificity. This is also the case with chitin-like substrates. For example, in man both chitotriosidase and AMCase can degrade chitin and chito-oligomers. Moreover, it can be speculated that also lysozyme or hitherto unidentified enzymes can hydrolyse chito-oligomers. Indeed, in serum of individuals that are homozygous for the 24 bp duplication in the chitotriosidase gene a residual enzyme activity can be detected. This is not due to chitotriosidase but should be ascribed to another enzyme. Another serious complication is formed by infections. For example, during aspergillosis fungal chitinases are released in the circulation that is also able to hydrolyse chito-oligomer substrates.

Because of this phenomenon, it is sometimes troublesome to identify one specific enzyme on the basis of enzymatic assays solely.

The invention therefore also provides a method wherein the endoglycosidase is at least partially isolated from a sample before a substrate of the endoglycosidase is provided. In this case, enzymatic activity can be better correlated to the amount of the specific enzyme. In the art many techniques for isolating an enzyme from a sample are known. Preferably, an endoglycosidase is isolated from a sample by a proteinaceous molecule capable of specifically binding the endoglycosidase. The proteinaceous molecule for instance comprises an antibody or a functional part, derivative and/or analogue thereof. The antibody or functional part, derivative and/or analogue thereof can be bound to a carrier. After incubation with a sample, the sample can be washed away, removing unbound enzymes present in the sample which may have overlapping substrate specificity as the bound endoglycosidase. After this washing step, activity of the bound endoglycosidase can be determined with a method of the invention.

In one aspect the invention provides a use of a molecule capable of being glycosylated by an endoglycosidase for at least partly inhibiting the transglycosidase activity of the endoglycosidase. As is explained before, the presence of the molecule can reduce the chance of the substrate of becoming transglycosylated. Preferably, the molecule comprises an oligosaccharide.

In yet another aspect the invention provides a compound having the formula R1-Sugar X-Sugar Y, wherein Sugar Y is a monosaccharride or an oligosaccharide, Sugar X is the non-reducing end monosaccharide, and R1=H or O—CH3, wherein R1 is bound to the C4 carbon atom of the non-reducing end monosaccharide.

In yet another aspect the invention provides a compound having the formula R1-Sugar X-Sugar Y, wherein Sugar Y is a monosaccharride or an oligosaccharide, Sugar X is the non-reducing end monosaccharide, and R1=H, wherein the C4 carbon atom of the non-reducing end monosaccharide is replaced by a sulphur atom and R1 is bound to the sulphur atom.

Preferably the non-reducing end monosaccharide comprises N-acetylglucosamine.

Such compound of the invention is particularly suitable for use in a method of the invention. In one embodiment the compound comprises a leaving group. Preferably the leaving group comprises methyl-umbelliferyl, para-nitrophenyl, fluorescein, or a functional part, derivative and/or analogue thereof. The leaving group is preferably located at the end of the oligosaccharide opposite the non-reducing end. Thus in the case where there are two sugar moieties on the sugar Y. In case where sugar Y is an oligosaccharide, (i.e. of formula R1-Sugar X-Sugar1-Sugar2) the leaving group is preferably on Sugar2, and so on for oligosaccharides having 3 or 4 sugars.

A substrate of the invention is very suitable for the preparation of a kit for detecting an activity of an endoglycosidase. Hence the invention also provides a use of a substrate of an endoglycosidase, the substrate comprising an oligosaccharide wherein a hydroxyl group in the non-reducing end sugar moiety is removed for the preparation of a kit for detecting an activity of an endoglycosidase. A kit for detecting an activity of an endoglycosidase comprising a substrate of an endoglycosidase the substrate comprising an oligosaccharide wherein a hydroxyl group in the non-reducing end sugar moiety is removed is also herewith provided. Preferably the hydroxyl group is substituted by a hydrogen atom or a methoxy moiety.

Also herewith provided is a kit for detecting an activity of an endoglycosidase comprising a substrate of an endoglycosidase the substrate comprising an oligosaccharide wherein a carbon atom in the non-reducing end sugar moiety and a hydroxyl group bound to the carbon atom are substituted by an SH group, as well as a kit for detecting an activity of an endoglycosidase comprising a substrate of an endoglycosidase and another molecule capable of being glycosylated by the endoglycosidase. Preferably the molecule comprises an alternative oligosaccharide.

In a further embodiment a kit of the invention further comprises a proteinaceous molecule capable of specifically binding the endoglycosidase. With such a proteinaceous molecule it is possible to at least in part isolate the endoglycosidase from a sample. This way, influence of an enzyme with overlapping substrate specificity upon a measurement of enzyme activity of the endoglycosidase can be reduced, as explained before.

A method of the invention can be used in the clinic for several diagnostic applications. For instance, in the setting of a bladder cancer test a non-invasive method of the invention for detecting hyaluronidase activity will be a great step forward compared to the current gold standard of cytoscopy. Another application of a hyaluronidase activity assay of the invention is to measure the sperm function together with the acrosomal intactness (AT) score in infertile men, since both are considered to be good indicators of sperm function (Tambe et al., 2001). The invention therefore provides a use of a kit according to the invention for the diagnosis of infertility.

Furthermore, an interesting hypothesis by Desoize et al. (2000) is that hyaluronidase increases drug potency in cancer patients by decreasing multicellular resistance. In addition, Lin et al. (2001) assume that testicular hyaluronidase (PH20), used as adjuvant in chemotherapy, enhances drug permeability. To monitor the therapy in the clinic a simple assay of the invention for hyaluronidase activity is useful.

Heparanase activity can be measured by a method of the invention as well. Such assay can be easily applied for surveillance in anticoagulant therapy, as diagnostic tool in cancer staging and for scientific research on the controversy about the molecular and biochemical properties of the mammalian gene family heparanase.

Hence, in one aspect the invention provides a use of a kit according to the invention for the diagnosis of a disease wherein an altered amount of an endoglycosidase is involved. As the amount of endoglycosidase can change during different stages of a disease, or during treatment of a disease, the invention also provides a use of a kit of the invention for the determination of the status of a disease wherein an altered amount of an endoglycosidase is involved. Additionally, the invention provides a use of a kit of the invention for monitoring a treatment of a disease wherein an altered amount of an endoglycosidase is involved. In one embodiment the disease comprises lysosomal storage disease, chronic inflammation, sepsis, thalassemia, and/or bladder cancer (such as for instance Gaucher disease, Sarcoidosis, multiple sclerosis, arthritis, and Crohn's disease).

In yet another aspect the invention also provides a method for diagnosing infertility, comprising detecting an activity of an endoglycosidase in a sample of an individual with a method according to the invention and comparing the activity with a reference value.

Also provides is a method for diagnosing a (status of a) disease wherein an altered amount of an endoglycosidase is involved, comprising detecting an activity of an endoglycosidase in a sample of an individual with a method according to the invention and comparing the activity with a reference value.

According to the present invention, transglycosidase activity of an endoglycosidase is significant. Therefore, contrary to what was currently assumed, an endoglycosidase is very suitable for the generation of a substrate. The invention therefore provides a method for generating a substrate, comprising:
  providing an endoglycosidase with a sugar moiety and a molecule capable of being transglycosylated, and
  removing formed substrate. Preferably the endoglycosidase comprises a chitinase, mucinase, lysozyme, heparanase, hyaluronidase, cellulase and or glucanase.

Areas of application of CHIS1 substrate and CHI-kit.

Our finding that CHIS1 is a superior substrate for all chitinases tested indicates a broad area of application. As described in the introduction chitinases are of interest in numerous fields, including the diagnosis and monitoring of pathological conditions. After the discovery of the marked elevation in plasma chitotriosidase in Gaucher patients it was investigated by us what the precise origin of the excessive plasma enzyme is. Our studies revealed that the pathological lipid-laden macrophages (Gaucher cells) themselves synthesize and secrete massively chitotriosidase into the circulation. Firstly, in samples of spleens of symptomatic Gaucher patients the levels of glucosylceramide, which are a direct measure of the amount of Gaucher cells, correlate strictly with chitotriosidase activity levels. Secondly, in situ hybridisation with a specific chitotriosidase RNA probe showed massive labeling of Gaucher cells in liver, spleen, marrow and lung. The excessive chitotriosidase in plasma of Gaucher patients therefore originates from the pathological Gaucher cells in various tissues.

The discovery that activated storage macrophages are the source of the excessive plasma chitotriosidase in Gaucher patients, made us conceive that besides Gaucher disease several other disease conditions in which activated neutrophils and/or macrophages are involved might show detectable chitotriosidase abnormalities that can be exploited for diagnosis as well as for monitoring and optimalization of therapeutic intervention. We and others have indeed meanwhile observed that the enzyme is elevated under specific disease conditions, usually associated with demonstrated involvement of chronically activated macrophages. Examples are sarcoidosis, arthritis, Leishmaniasis, thalassemia, HES (hydroxyethyl-starch)-induced p runitis, CGD (chronic granulomatosis disease), Crohn's disease, Tangier disease, atherosclerosis and several lysosomal lipid storage disorders (Hollak et al, 1994; Guo et al., 1995; Barone et al., 1999; Boot et al., 1999; unpublished observations Aerts J. M. F. G.).

Application of chititotriosidase to monitor disease as illustrated by some examples 1. Gaucher disease. Gaucher disease is an inherited disorder characterized by the accumulation in tissues of glucosylceramide-laden macrophages ('Gaucher cells') as the result of a deficiency in the lysosomal enzyme glucocerebrosidase. The presence of Gaucher cells is responsible for the common symptoms in Gaucher patients, such as hepatomegaly, splenomegaly, and skeletal deterioration. The clinical manifestations in glucocerebrosidase-deficient individuals are very heterogeneous. Onset of clinical symptoms may occur at very young age, but the disorder may also remain virtually asymptomatic. Accurate prediction of disease severity and progression is not possible on the basis of the mutant glucocerebrosidase genotype of Gaucher patients.

During our search for sensitive markers for the presence of Gaucher cells, we firstly discovered that in plasma of symptomatic patients chitotriosidase activity is markedly elevated (Hollak et al, 1994). Our present experience with more than 700 symptomatic Gaucher patients indicates that the average plasma chitotriosidase activity is about 1000-fold higher than the normal mean. Several other researchers have meanwhile confirmed our findings. Plasma chitotriosidase measurement is now internationally used for the diagnosis of Gaucher disease (Aerts et al, 1997). The measurement of plasma or serum levels is also growingly applied for the diagnosis of other inherited lysosomal storage disorders in man (see Guo et al, 1995; vom Dahi et al.1999, Chamoles et al., 2002).

FIG. 6 shows a comparison of plasma chitotriosidase activity data for a group of 25 Gaucher disease type I patients using the old standard method (4MU-chitotriose as substrate at 27 microM) and the novel method (4MU-4-deoxy-chitobiose as substrate at 150 microM).

Deficiency in chitotriosidase activity can be observed in specific individuals. About 5% of all subjects, including Gaucher patients, shows no true chitotriosidase activity due to the homozygous presence of a mutant chitotriosidase gene. About 35% of all individuals are carrier for this chitotriosidase defect. Chitotriosidase activity levels in materials (j~1asma, leukocytes, urine) of carriers are on average half those in control materials (Boot et al., 1998; Giraldo et al., 2001). Therefore, the interpretation of chitotriosidase activity levels without information on the chitotriosidase genotype of an individual is difficult. For example, the mean plasma chitotriosidase activity was 35.6 nmol/ml. hour in the case of 50 normal subjects with a wildtype chitotriosidase genotype and 19.7 nmol/ml. hour in the case of 50 age- and sex-matched normal subjects that were carrier for the chitotriosidase mutation. The mean plasma chitotriosidase activity was 17.540 nmol/ml. hour in the case of 30 type 1 Gaucher patients with a wildtype chitotriosidase genotype and 9.034 nmollml. hr in the case of 30 clinically comparable patients that were carrier for the chitotriosidase mutation. These findings illustrate clearly that in order to interpret the values on chitotriosidase activity level in an individual the chitotriosidase genotype has to be taken into account and thus needs to be determined. This determination can be performed by detection of the presence of the 24 bp duplication in the chitotriosidase gene. Consequently, there has been a need for a convenient method that allows accurate identification of the chitotriosidase genotype of an individual. Such a method has recently been developed by us.

In daily practice the demonstration of a very low plasma chitotriosidase activity (less than 5 nmol/ml.hour) for an individual constitutes a problem. This may either point to a chitotriosidase deficiency in combination with elevated plasma lysozyme activity or due to carriership of the chitotriosidase gene duplication. In the former case, it may not be interpreted from the result that the individual is not suffering from Gaucher disease (or another disorder involving chronically activated macrophages). If leukocytes are available a distinction can be rapidly made between the two possibilities by the analysis of the chitotriosidase genotype. Unfortunately in daily practice such material is not always available. The CHI-kit offers a convenient solution since it allows a distinction between enzyme activity exerted by chitotriosidase versus enzyme activity related to other endoglucosaminidases.

Besides its use in the confirmation of the diagnosis of Gaucher disease, the measurement of plasma chitotriosidase activity is extremely valuable in decision making regarding initiation of costly therapeutic intervention and optimizing treatment dosing regimens (Aerts et al, 1997; Young et al., 1997; Cox et al., 2000). FIG. 7 shows the responses in plasma chitotriosidase of the first European Gaucher patient treated with enzyme supplementation and substrate deprivation, both in the Academic Medical Centre of the University of Amsterdam. FIG. 8 shows as an example the plasma chitotriosidase levels in two sisters suffering from Gaucher disease (homozygotes for the L44P glucocerebrosidase mutation). It can be seen that onset of disease can be accurately monitored by monitoring plasma enzyme level. Initiation of therapy results in reductions of the plasma marker of the pathological Gaucher cells. Attempts to reduce the dose of therapeutic enzyme resulted in both girls in a relapse as revealed by increases in their plasma chitotriosidase. In many countries regular measurement of plasma chitotriosidase is now used to monitor response to therapy and increases in plasma chitotriosidase levels are used as a criterion to initiate treatment. The plasma chitotriosidase now plays an important role in the clinical management of Gaucher patients. The European Working Group on Gaucher Disease has recommended its use.

FIG. 9 shows an example of monitoring plasma chitotriosidase changes in a Gaucher patient following enzyme therapy. Depictured are results obtained with the old 4MU-chitotriose substrate and with the novel 4MU-chitobiose substrate. It has to be noted that with the old substrate the measurements had to be performed at 4 different plasma dilutions in order to be sure that activity was proportional to enzyme concentration. With the novel substrate a single measurement was sufficient.

Sarcoidosis: Diagnosis and Therapy. Sarcoidosis is a disease of unknown etiology in which activated mononuclear phagocytes and T-lymphocytes are involved in formation of granulomas. In sarcoidosis, granulomas develop in a variety of organs, most commonly the lungs, lymph nodes, bone, nervous tissue and skin. Activity of sarcoidosis has been defined by clinical features, accompanied by elevated levels of several plasma factors that are usually found in association with activated macrophages or T-lymphocytes. Macrophage associated factors include angiotensin converting enzyme (ACE), lysozyme, sCD14, calcitrol, neopterin and sTNF receptors. ACE determination is the most widely used laboratory test for sarcoidosis. However, ACE values have an estimated sensitivity of only 57%. Especially in the first months of acute disease, ACE levels may be normal.

The diagnostic value of chitotriosidase for sarcoidosis was investigated. Patients with sarcoidosis show elevated plasma chitotriosidase activity levels. The increase is much more spectacular as that in corresponding ACE levels The levels of ACE were elevated in 28 of 32 patients (median 90/U/i, range 26-282 U/i; normal range 18-55 U/l). Chitotriosidase was not deficient in any of the patients and elevated in all (median 577 nmol/ml.h, range 74-3032 nmol/ml.h, normal range<70 nmol/ml.h).

After completion of our study we did observe one sarcoidosis patient with chitotriosidase-deficiency. The extent of elevation in plasma chitotriosidase seems to correlate with severity of disease manifestation. We have been able to demonstrate by in situ hybridisation that the abnormal macrophages (epitheloid cells) in bronchoalveolar lavage fluid (BALF) of sarcoidosis patients contain large amounts of chitotriosidase RNA. Moreover, BALF of sarcoidosis patients shows high levels of chitotriosidase activity: control median concentration was 0.54 nmol/ml. h (range 0.32-1.67) and the calculated epithelial lining fluid (ELF) value was 53.2 nmol/ml.h (range 17.6-123.9). In the sarcoidosis patients the median concentration was 49.4 nmol/ml.h (range 0.72-468.9) for BALF and 1497.5 nmol/ml. h (range 67.3-33438) for ELF. The measurement of plasma chitotriosidase activity, in combination with determination of chitotriosidase genotype, allows sensitive detection of clinical manifestation of sarcoidosis. Importantly, clear increases in plasma chitotriosidase were not observed in plasma of patients suffering from lymphomas (n=24) and leprosy (n5). Chitotriosidase levels in plasma of untreated patients with pulmonary tuberculosis were slightly elevated in 7 of 12 patients (median 78.7 nmol/ml.h, range 8.2-147 nmol/ml.h). As compared to patients with sarcoidosis these levels were significantly lower. Thus, the relative simple and convenient chitotriosidase determination is extremely useful in the differential diagnosis of sarcoidosis.

Therapy

Sarcoidosis is treated by administration of corticosteroids. Determination of optimal drug dosage is critical but unfortunately also complicated. It was studied whether plasma chitotriosidase levels change upon treatment. The chitotriosidase activity in a patient that received orally 25 mg of prednisone markedly decreased. However, tapering of the dose to 5 mg per day after 17 weeks was followed by recurrence of disease activity while chitotriosidase activity increment preceded the worsening of symptoms. Another interesting finding concerns a patient that was treated with corticosteroid pulse therapy (1000 mg methyiprednisone for three days every 2 weeks). His chitotriosidase level before the initiation of treatment was very high, and it rapidly declined after the institution of corticosteroids. This was accompanied by marked clinical improvement. The findings show that plasma chitotriosidase is an extremely useful guideline for diagnosis and optimalization of anti-inflammatory treatment of acidosis.

Multiple Sclerosis: Diagnosis and Therapy

Multiple sclerosis (MS) is a presumed T-cell mediated Thi type autoimmune disease. In the pathophysiology of multiple sclerosis (MS) an important role is envisioned for activated T-lymphocytes and macrophages. It is generally thought that macrophages and resident brain microglia are agents of the demyelization that occurs in MS. Chitotriosidase activity was determined in plasma and cerebral spine fluid (CSF) of MS patients. In CSF of patients, but not in plasma, chitotriosidase activity is clearly elevated in relation to manifestation of MS. In a MS patient receiving recombinant beta-1B interferon treatment a concomitant 10-fold reduction in CSF chitotriosidase was noted by us. These findings indicate that chitotriosidase measurement is useful to assess the presence of activated phagocytes in the brain of MS patients and correction therein following treatment.

Arthritis

Arthritis is characterized by inflammation of joints and an important role for activated phagocytes in the pathophysiology is generally assumed. We investigated chitotriosidase activity in plasma and synovial fluid samples of patients with arthritis. In arthritis plasma chitotriosidase activities tend to be above the normal value. In plasma of some patients very high levels have been observed, exceeding 1000 mol/h/ml. In sensorial fluid of arthritis cases a very high enzyme activity is demonstrable. The efficacy of anti-inflammatory treatment that aims to de-activate phagocytes in arthritis patients can be determined by analysis of chitotriosidase levels.

Crohn's Disease

Crohn's disease (enteritis regionalis) is characterized by chronic granulomatous inflammation of the duodenum and colon. Activated T-lymphocytes and a Thb 1-like profile of cytokine production are responsible for macrophage activation and release of anti-inflammatory cytokines, toxic oxygen metabolites and nitric oxide which maintain the intestinal Thi-type response. Chitotriosidase activities in untreated patients with active Crohn's disease (n=5) were slightly (mean: 3.2 fold) elevated above the normal value. High chitotriosidase activity was detected in intestinal biopsies of a Crohn's disease patient, being more than 20 fold that in corresponding control material. The findings show that the sequential measurement of plasma chitotriosidase represent a non-invasive method to assess Crohn's disease activity and response to anti-inflammatory treatment.

Neutrophil Activation. To test the potential of chitotriosidase as a marker for the release of specific granules of neutrophils, we examined samples obtained in earlier studies in which granulocyte colony stimulating factor (G-CSF) or granulocyte-macrophage colony stimulating factor (GM-CSF) were administered to healthy volunteers. In these experiments it was previously shown that degranulation of the specific granules of neutrophils occurs. Neutrophils release their specific granule content after 2 hours after G-CSF injection, as detectable by the appearance of lactoferrin in the circulation. Parallel increases in serum chitotriosidase levels are found. The increase in lactoferrin and chitotriosidase is not due to an increase in neutrophil cell number, because these levels peak later in time, after about 12 hours. A second peak in lactoferrin and chitotriosidase levels is seen after 6 to days after G-CSF injection. This is most likely caused by the turnover of the large amount of cells formed after G-CSF induction. Administration of GM-CSF gave similar results (not shown) except for the second peak which was not present. The findings show that plasma chitotriosidase can be used to detect activation (that is, degranulation) of neutrophils, as for example induced with G-CSF or GM-CSF.

Infections.

Measurement of plasma chitotriosidase levels appears also of interest in connection to (susceptibility) for infections. Abnormalities in plasma chitotriosidase have been noted in connection to fungal infections in neonates (Labadaridis et al., 1998), and following administration of LPS to chimpanzees. (Lauw et al., 1999). Chitotriosidase deficiency, detectable by the total absence of plasma chitotriosidase activity using the CHI-kit, has recently been reported to impose an increased risk for specific tropical infections (Choi et al., 2001).

BRIEF DESCRIPTION OF THE DRAWINGS

FIG. 2A. Transglycosylation by chitotriosidase. Explanation for the outcome of the experiment depicted in FIG. 2. Chitotriosidase is able to remove chitobiose-unit from PNP-chitobiose, resulting in release of PNP that is spectrometrically detected. (FIG. 2 panel A). Chitotriosidase is not able to remove N-acetylglucosamine from 4MU-hexosamine, causing no release of fluorescent 4MU from 4MU-hexosamine (FIG. 2 panel B). The chitobiose-unit released by chitotriosidase from PNP-chitobiose can be accepted by either water molecules or by C4-hydroxyl of 4MU-hexosamine. The latter reaction results in formation of 4MU-chitotriose that subsequently can be hydrolyzed to chitotriose and fluorescent 4MU (FIG. 2 panel C). The reaction mechanisms explain the slow formation of fluorescent 4MU after a lag phase during the incubation of recombinant chitotriosidase with the mixture of 4MU-hexosamine and PNP-chitobiose.

FIG. 9A. Stimulation of enzyme assay by the presence of an acceptor.

FIG. 11. Structures of compounds of the instant invention.

BEST MODE OF THE INVENTION

EXAMPLES

Example I

Figure 1:
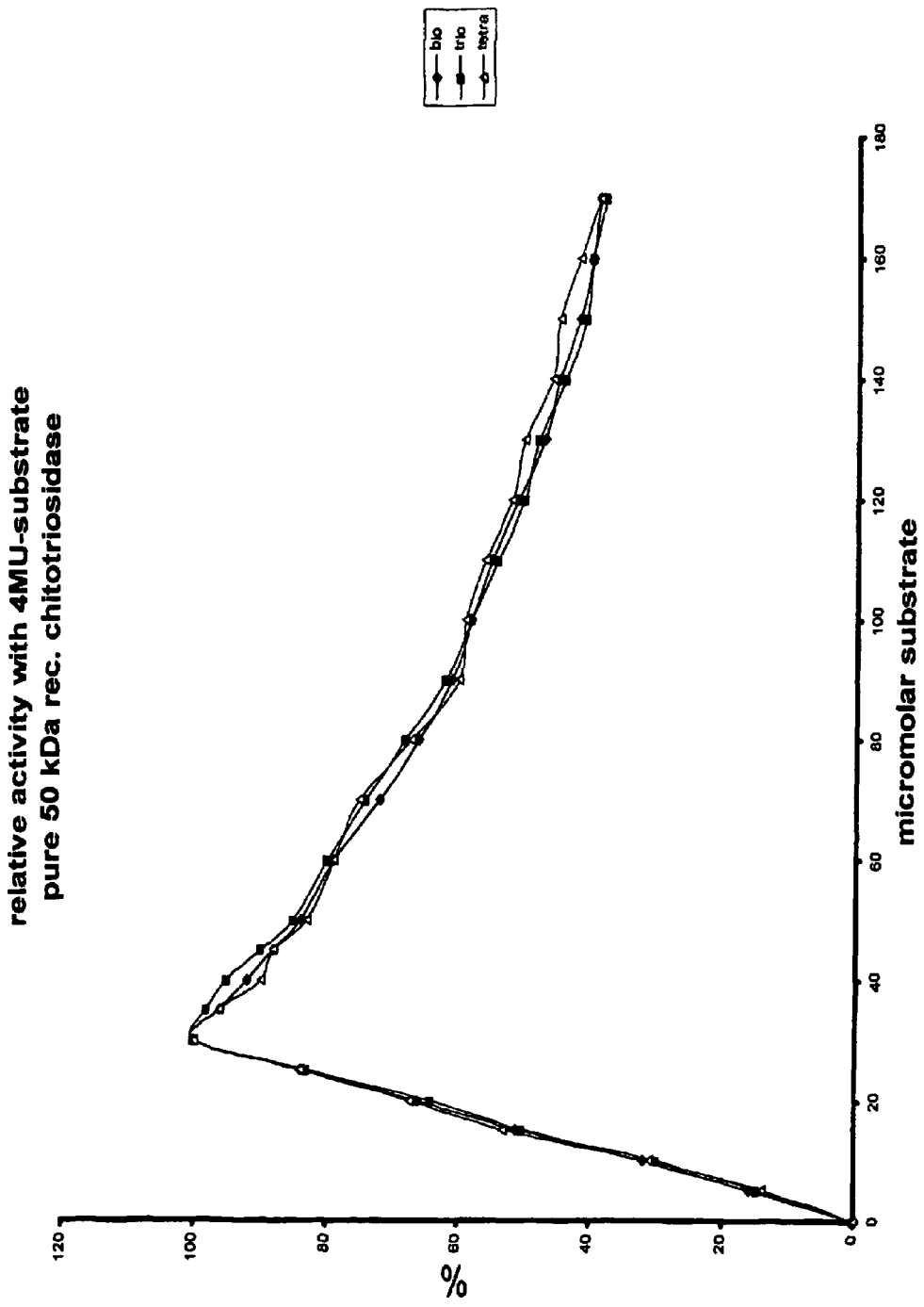
FIG. 1. Apparent substrate inhibition of chitotriosidase. Activity of recombinant 50 kDa human chitotriosidase towards 4MU-chitobiose, chitotriose and chitotetraose substrates. Substrate inhibition is dependent on absolute concentration of 4MU-chito-oligomers but not on their chemical composition. Recombinant 50 kDa chitotriosidase was produced exactly as described by Boot et al (1997). The 4MU-substrates were purchased from Sigma, St. Louis, USA. Enzyme reactions were performed as described in Hollak et. al (1994) with the exception that substrate concentration as varied.
Figure 2:
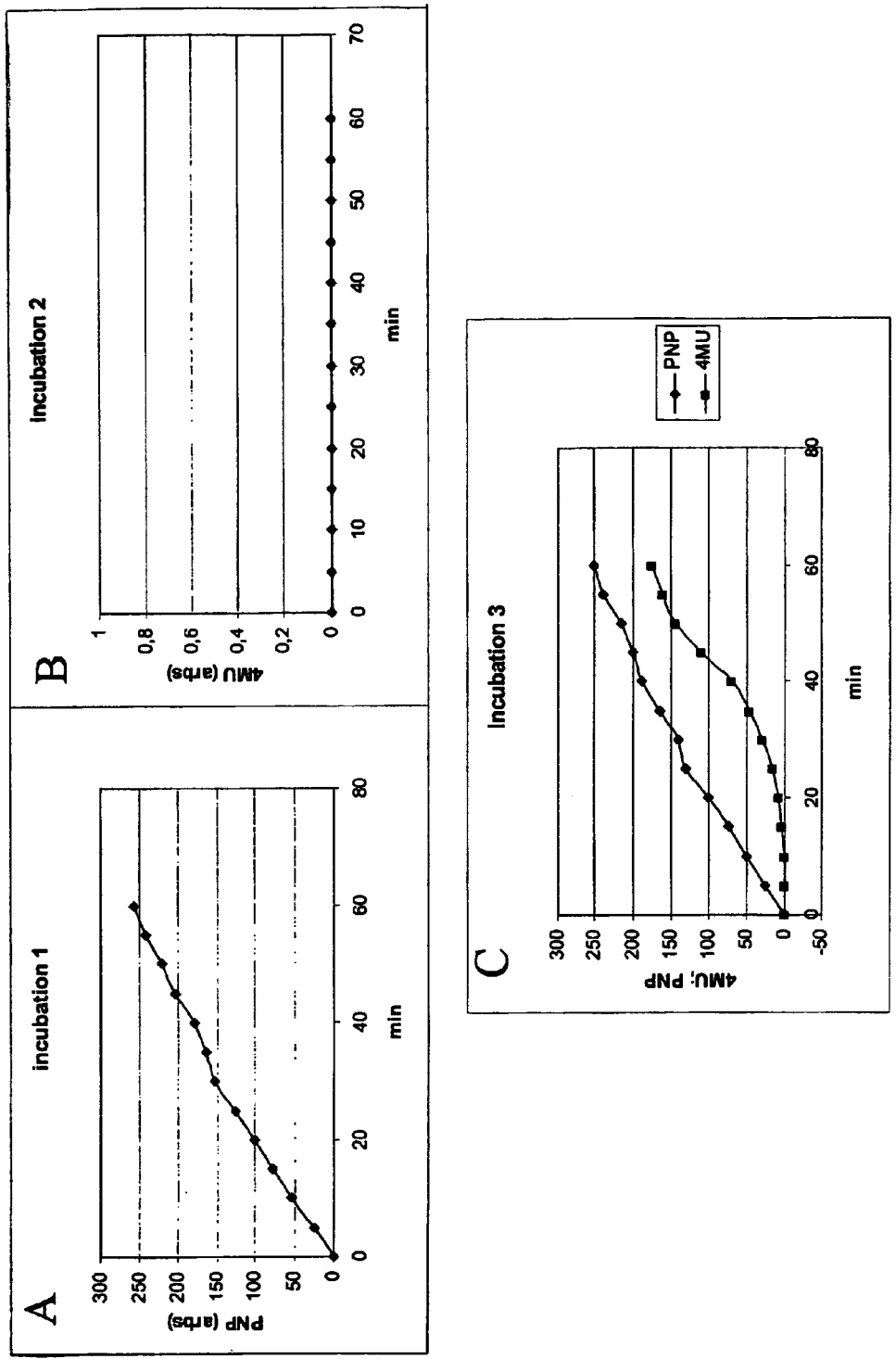
FIG. 2. Demonstration of catalysis of hydrolysis and transglycosylation by chitotriosidase. Activity of 50 kDa recombinant human chitotriosidase towards PNPchitobiose, 4MU-hexosamine and a mixture of both substrates. Panel A: incubation 1. Enzyme was incubated with 50 microM PNP-chitobiose and the reaction was stopped at indicated time points by adding excess of 0.2 M glycine-NaOH @H1O.3). Release of the hydrolysis product p-nitrophenol was determined spectrometrically at 405 nM. Panel B: incubation 2. Enzyme was incubated with 50 microM 4MU-hexosamine and the reaction was stopped at indicated time points by adding excess of 0.2 M glycine-NaOH (pH10.3). Release of the hydrolysis product 4-methyl-umbelliferone was determined fluorometrically (excitation at 366 nM; emission at 445 nM). Panel C: incubation 3. Enzyme was incubated with 50 microM PNPchitobiose and 50 microM 4MU-hexosamine and the reaction was stopped at indicated time points by adding excess of 0.2 M glycine-NaOH (pH10.3). Release of hydrolysis products was measured spectrometrically and fluoremetrically.
Figure 2B:
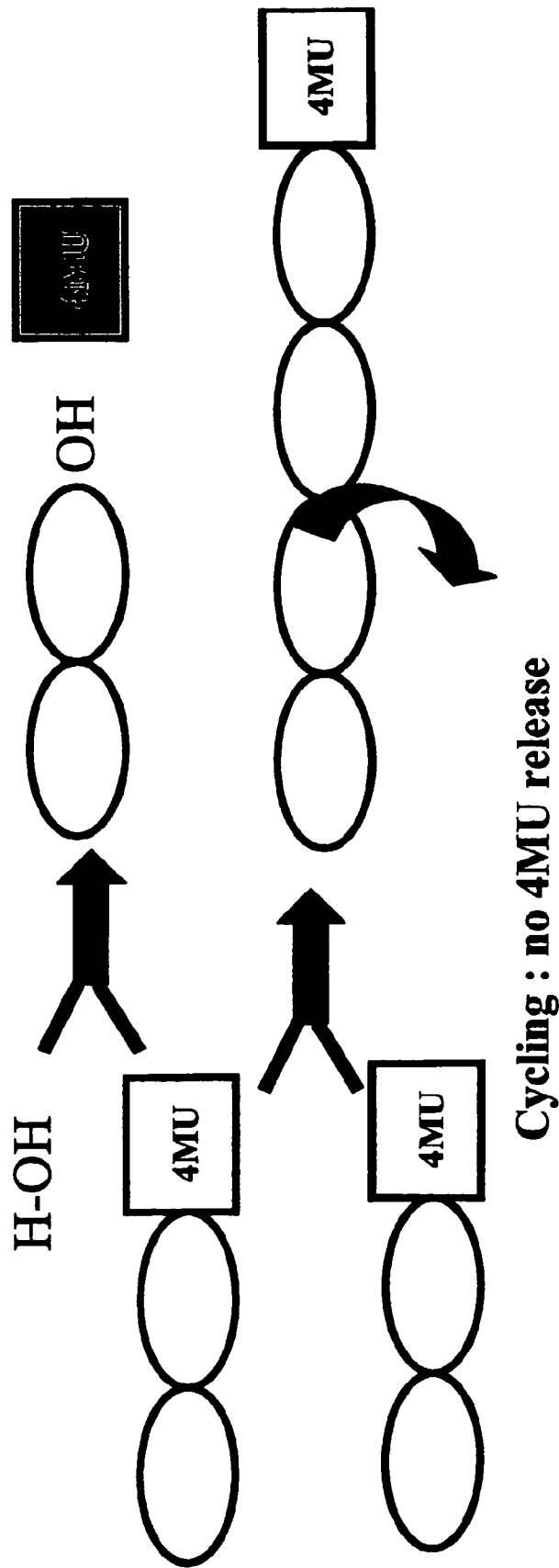
FIG. 2B. Transglycosylation as explanation for substrate inhibition with chito-oligomers. Transglycosylation is increased at higher substrate concentration resulting in increased futile cycling of chitobiose units between 4MU-chitobiose and 4MU-chitotetraose without release of detectable 4-methylumbelliferone.

It was investigated whether the terminal, non-reducing end N-acetylglucosamine 5 residues in the substrates could be directly involved in reactions catalysed by chitotriosidase. To test this, the following, seminal experiment was conceived. Pure chitotriosidase was incubated with 4-methylumbelliferyl-N-acetyiglucosamine (4-MU-hexosamine) alone (incubation 1), PNP-chitobiose alone (incubation 2) and a combination of both substrates (incubation 3). As expected, 4-MU-hexosamine is no substrate and therefore no fluorescent 4-MU is released during the incubation 1. In contrasts, PNP-chitobiose is a substrate and coloured PNP is formed during the incubation 2. Obviously, no fluorescent 4-MU is formed following incubation 2. During the first minutes of incubation only the colored PNP is formed, but surprisingly after some time there is also ongoing formation of the fluorescent 4-MU. (See FIG. 2).

The explanation for this remarkable phenomenon is depictured in FIG. 2A. Upon exposure of chitotriosidase to PNP-chitobiose and 4-MU-hexosamine there is formed the coloured PNP and via a transglycosylation reaction the chitobiose-unit is in part donated to 4MU-hexosamine. The latter process causes the gradual formation of 4-MU-chitotriose that is subsequently cleaved in chitotriose and the fluorescent 4-MU. In conclusion, the experiment elegantly revealed that chitotriosidase is not only capable of cleaving chito-oligomers using water molecules as acceptor but also donates the sugar moiety to another sugar as acceptor.

To further substantiate the transglycosylase activity of chitotriosidase we analyzed the products that are formed following incubation of enzyme with chito-oligomers. For this purpose, use was made of a fluorescent labeling of reaction products with ANS and their quantitative detection following gel electrophoresis with a Glycolmager, exactly according to the protocol suggested by the manufacturer Glyco. It was observed that chitopentaose (N-acetyiglucosamine 5-mer) is initially cleaved into chitobiose and chitotetraose. After some time however also chitotetraose is detectable, demonstrating the transfer of chitobiose units to existing free chitobiose units. This type of experiment renders direct and definitive proof for the capacity of chitotriosidase to act as transglycosylase.

Example II

Development of novel, superior substrates for measuring hydrolytic activity. After identifying the fact that the transglycosylase activity of chitotriosidase is instrumental to the problems encountered with 4-MU-chito-oligomer substrates, a way was searched to circumvent this complication. It was conceived that a substrate without the hydroxyl at the C-4 position in the non-reducing end N-acetylglucosamine could not act as acceptor. At the same time such modification should not interfere with the hydrolysis of the compound by chitotriosidase. The most attractive modification appeared an exchange of the C4-OH for —H, i.e. creating a deoxy-compound. It was envisioned that such type of compound should be the ideal substrate, being well hydrolyzed but being no acceptor for transglycosylation.

Figure 2C:
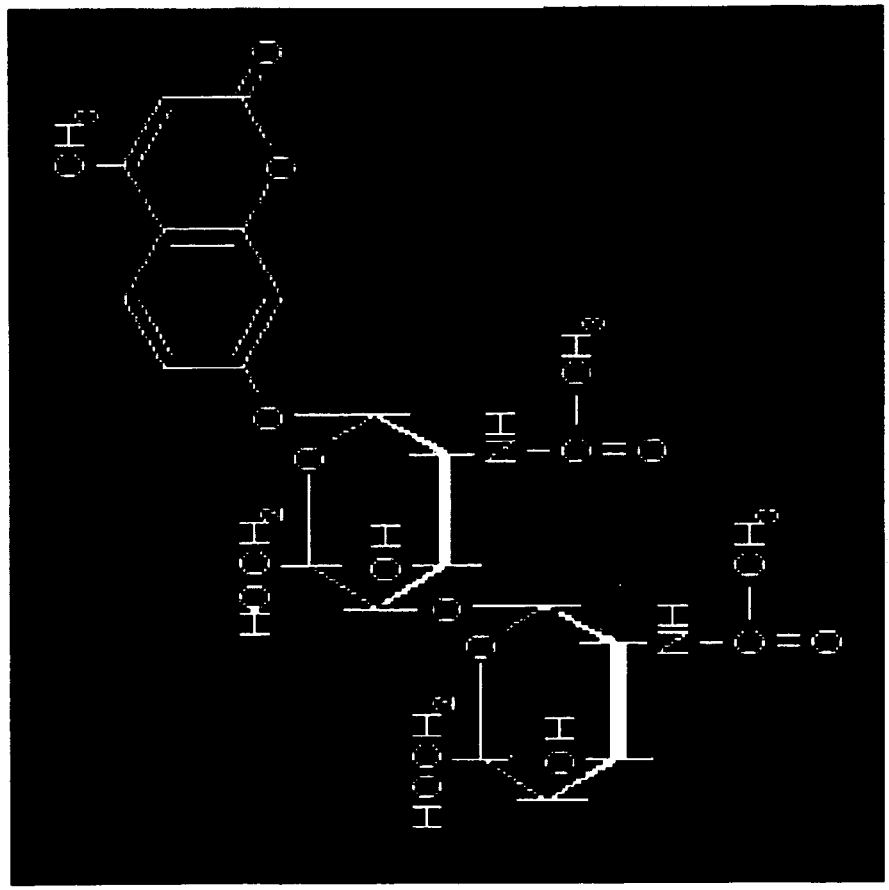
FIG. 2C. Structure of novel chitotriosidase substrate: 4-methylumbelliferyl-(4-deoxy)-chitobiose (CHIS1).

To test the value of this thought 4-MU-deoxychitobiose was synthesized, according to the synthesis pathway described in Example 4. The structure of the compound (4MU-deoxychitobiose CHIS 1) is depictured in FIG. 2C.

Figure 3:
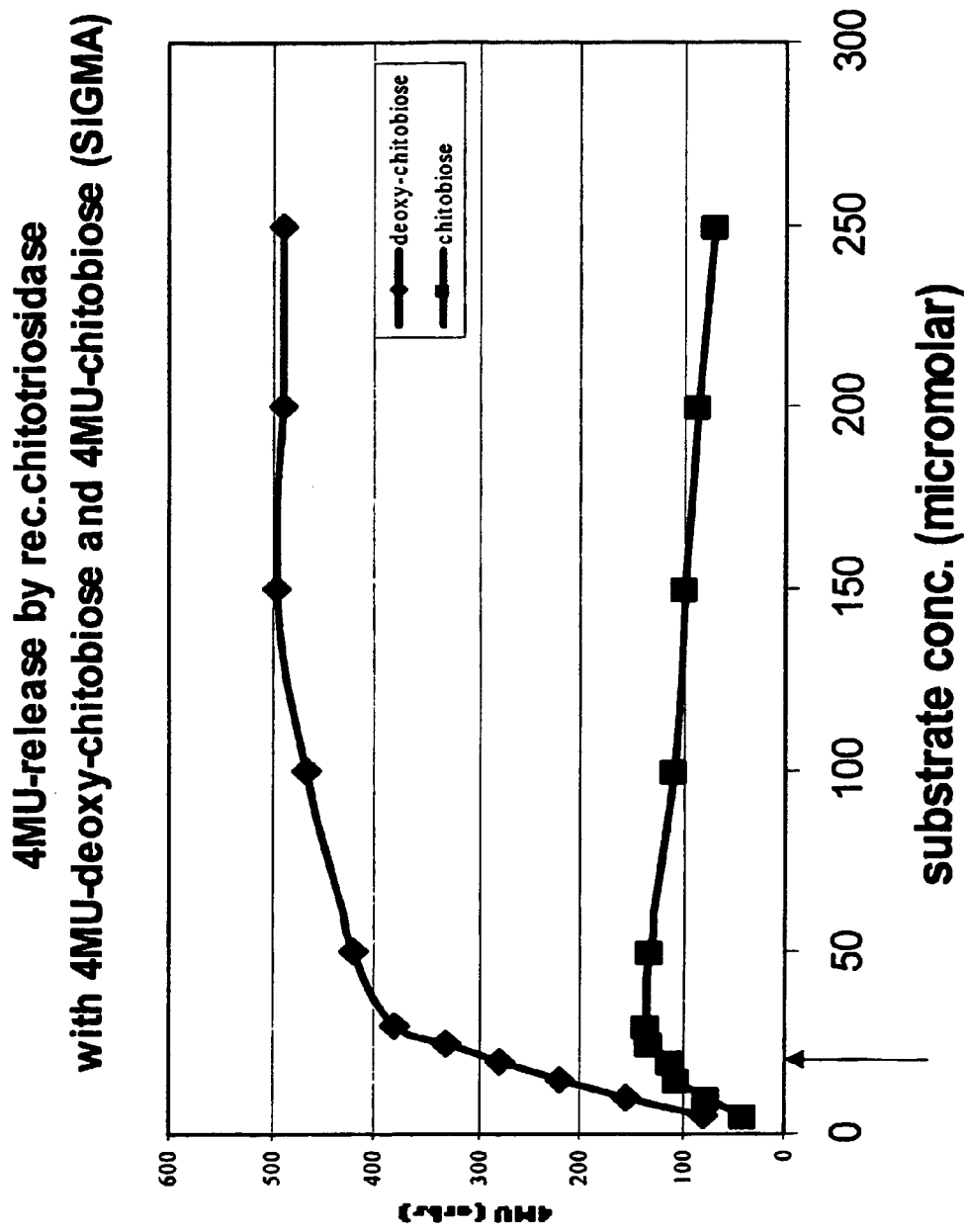
FIG. 3. Substrate concentration dependency of chitriosidase activity with novel artificial substrate as compared to present one. Activity of 50 kDa chitriosdase towards 4-MU-chitobiose and 4-deoxy-variant hereof (CHIS1). Enzyme was incubated at 37 C with indicated concentrations of substrates. Reactions were stopped after 10 minutes and 4-MU measured fluorometrically.

The CHISI compound was tested as substrate. For this purpose, pure 50 kDa chitotriosidase was incubated with this substrate at 37 C in Mclvaine buffer (pH 5.5). For comparison the enzymes were in parallel incubated with 4-MU-chitobiose (Sigma). The reaction was stopped by adding excess of 0.1 M glycine-NaOH @H 10.3) and fluorescence was monitored (excitation at 366 nm, emission at 445 nm). The result is shown in FIG. 3. It can be seen that CHIS1 does not show substrate inhibition.

Figure 4:
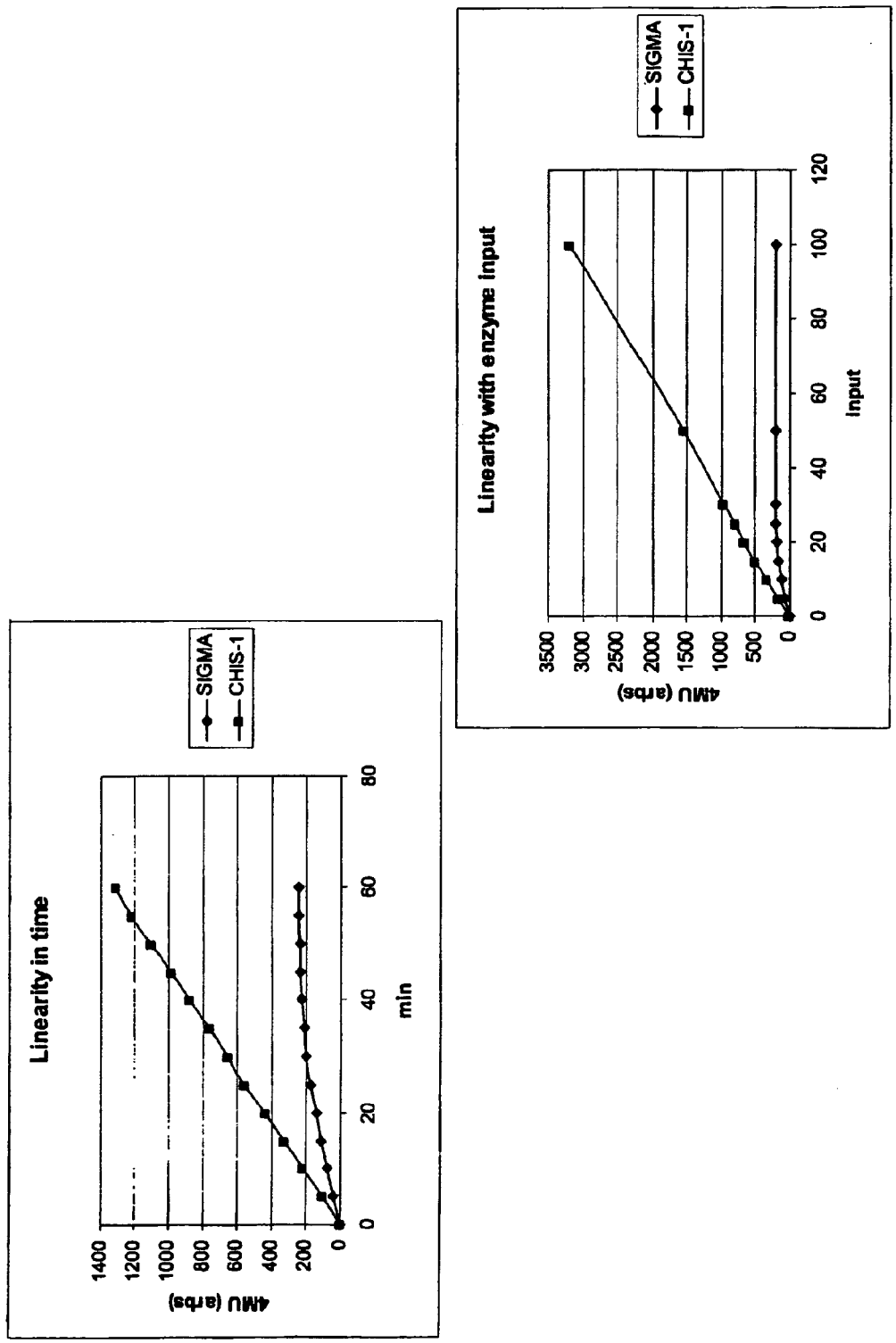
FIG. 4. Improved linearity of chitotriosidase assay with time and enzyme concentration. Activity of 50 kDa chitotriosdase towards 4-MU-chitobiose and 4-deoxy-variant hereof (CHIS). Reaction time (FIG. 5a) and concentration of enzyme (FIG. 5b) were varied and enzyme activity was measured with 4MU-chitobiose and 4-deoxy-variant hereof.

The sensitivity of detection of hydrolytic activity of chitotriosidase with CHIS1 is enormously improved compared to the 4-MU-chitobiose substrate (FIG. 4). Even more importantly, saturating substrate concentrations (100-200 microM) can be used in the case of CHIS (Km of chitotriosidase is 50 microM). This renders a great improvement with regard to reproducibility of the assay and interpretation of results. With the CHIS substrate the released 4MU is directly proportional with time and enzyme concentration in a broad range. This is intrinsically not the case for the 4MU-chitobiose substrate. Examples of linearity with time and enzyme input are depictured in FIG. 4.

It was next examined if CHIS is also a superior substrate for other chitinases. For this purpose, assays were performed with CHIS and 4-MU-chitobiose as substrate with bacterial chitinase (Sigma), purified recombinant 39 and 50 kDa forms of human and mouse chitotriosidase and AMCases and purified fetal calf serum chitinase. In all cases 4-MU-chitobiose showed apparent substrate inhibition at sub saturating concentrations whereas assays with CHIS were far more sensitive and linear at saturating substrate concentration (not shown). These results imply that CHIS has a broad applicability.

Example III

Figure 4A:
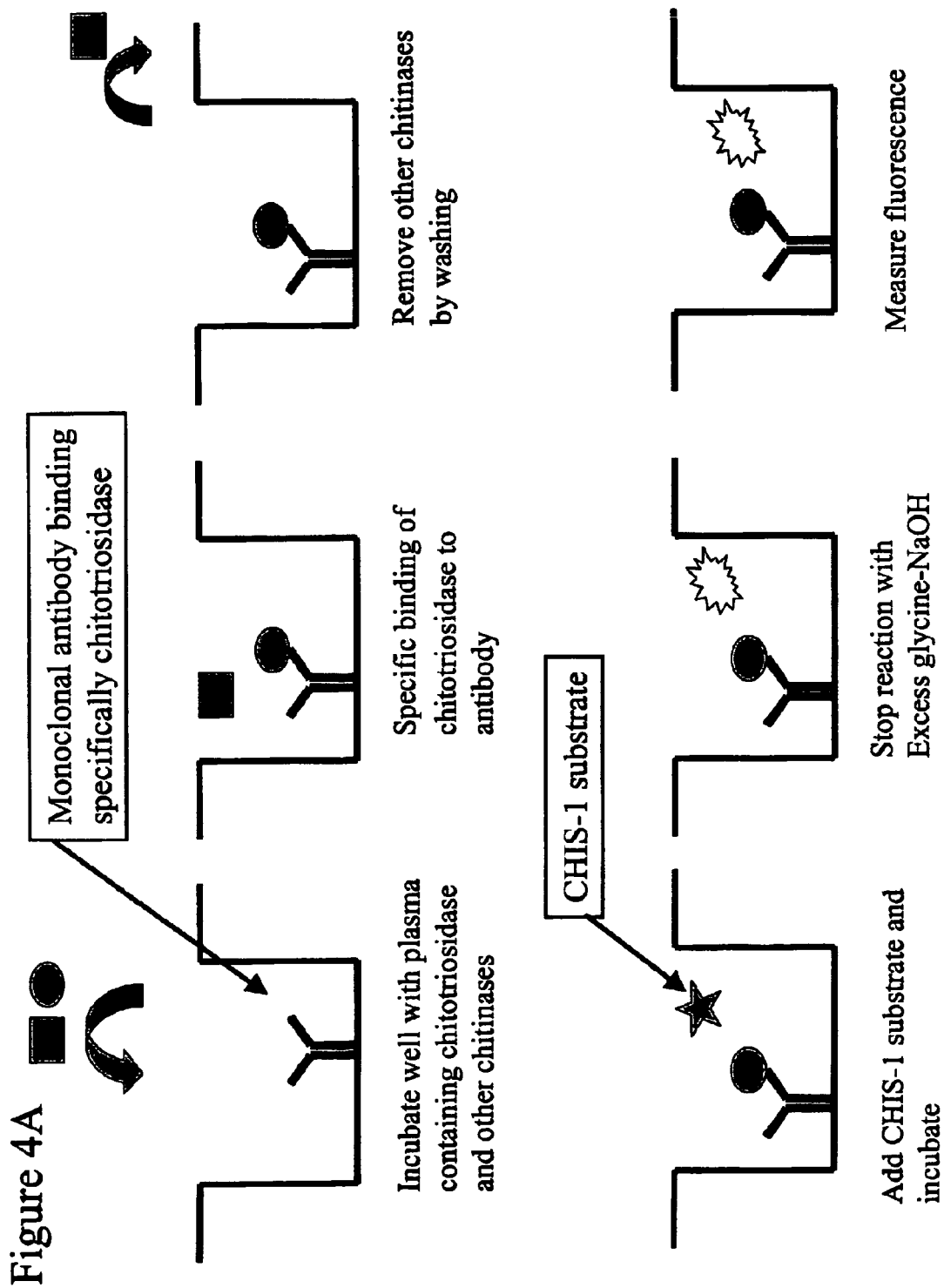
FIG. 4A. Principle of novel chitotriosidase microtitre plate assay: CHI-kit.

Use of CHIS and specific anti-chitotriosidase monoclonal antibody to detect chitinase activity in plasma/serum samples and other complex biological materials. We envisioned that an enormous improvement in the true measurement of enzymatic activity of chitotriosidase could be made by generating a specific monoclonal antibody towards chitotriosidase that allows immobilization of enzyme without interference with enzymatic activity. In this manner a microtiter plate well assay (CHI-kit) could be developed that allows reliable and selective measurement of chitotriosidase. See FIG. 4A.

Using conventional techniques and recombinant 39 kDa chitotriosidase as antigen, mice were immunized and hybridoma's were obtained. We screened successfully for production of monoclonal antibodies with the desired, above described, features.

Next in wells of microtiter plates monoclonal antibody was immobilised. After removal of non-adherent antibody the wells were incubated with serum/plasma samples. All chitotriosidase activity was bound by the immunosorbent as checked by analysis of residual enzyme activity in the supernatant. Next, the wells were washed and incubated with assay mixture containing CHIS. The reaction was stopped by adding excess glycine-NaOH (p H 10.3) and fluorescence was measured in a LS-50 Perkin Elmer fluorimeter.

Figure 5:
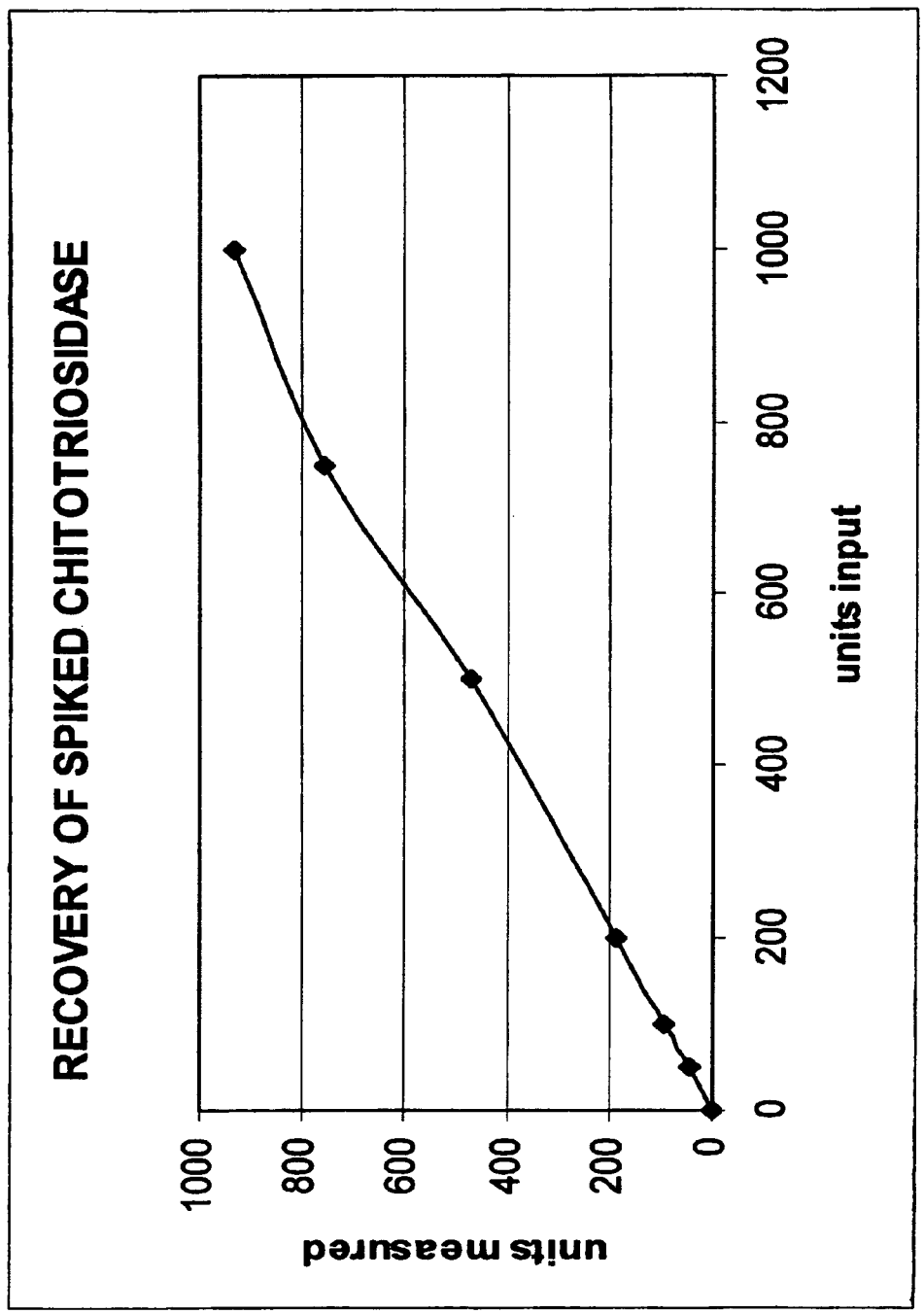
FIG. 5. Validation of immuno-linked chitotriosidase assay (CHI-kit). Detection of spiked recombinant cxhitotriosidase in chitotriosidase-deficient plasma sample. Excess of anti-chitotriosidase monoclonal antibody is linked to wells of microtiter plates. Wells are incubated for 30 mm with 100 microL of plasma sample of chitotriosidase-deficient individual in which was spiked increasing concentrations of recombinant 50 kDa chitotriosidase. After washing the wells were incubated with 120 microM CHIS, 50/100 mM McIlvaine buffer (pH 5.5) containing 1 mg/mi albumine. The reaction was stopped after 15 mm by adding 50 microL of 1.0 M glycine-NaOH. Fluorescence (excitation 366 nm; emission 445 nM) in the wells was measured. Expressed is the correlation between input of chitotriosidase and recovered enzyme activity.
Figure 6:
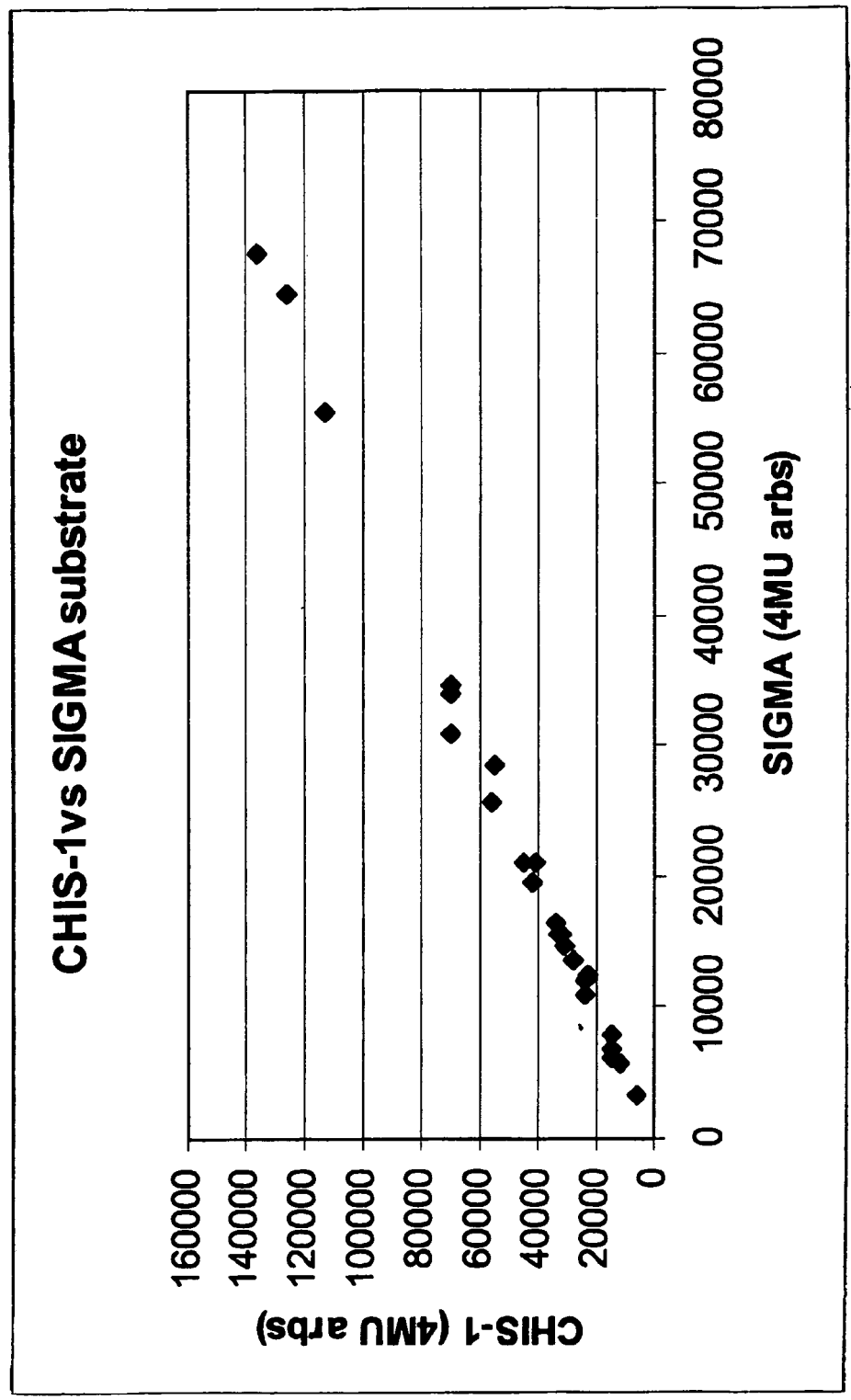
FIG. 6. Comparison of plasma chitotriosidase activity in 25 type I Gaucher patients measured with 4MU-chitotriose and the novel substrate CHI 1 (4MU-4-deoxy-chitObiOSe). Enzyme activity was measured with 27 microM 4MU-chitotriose (Sigma) or 150 microM CHIS-1. Other conditions were identical as described in Hollak et al., 1994.
Figure 7:
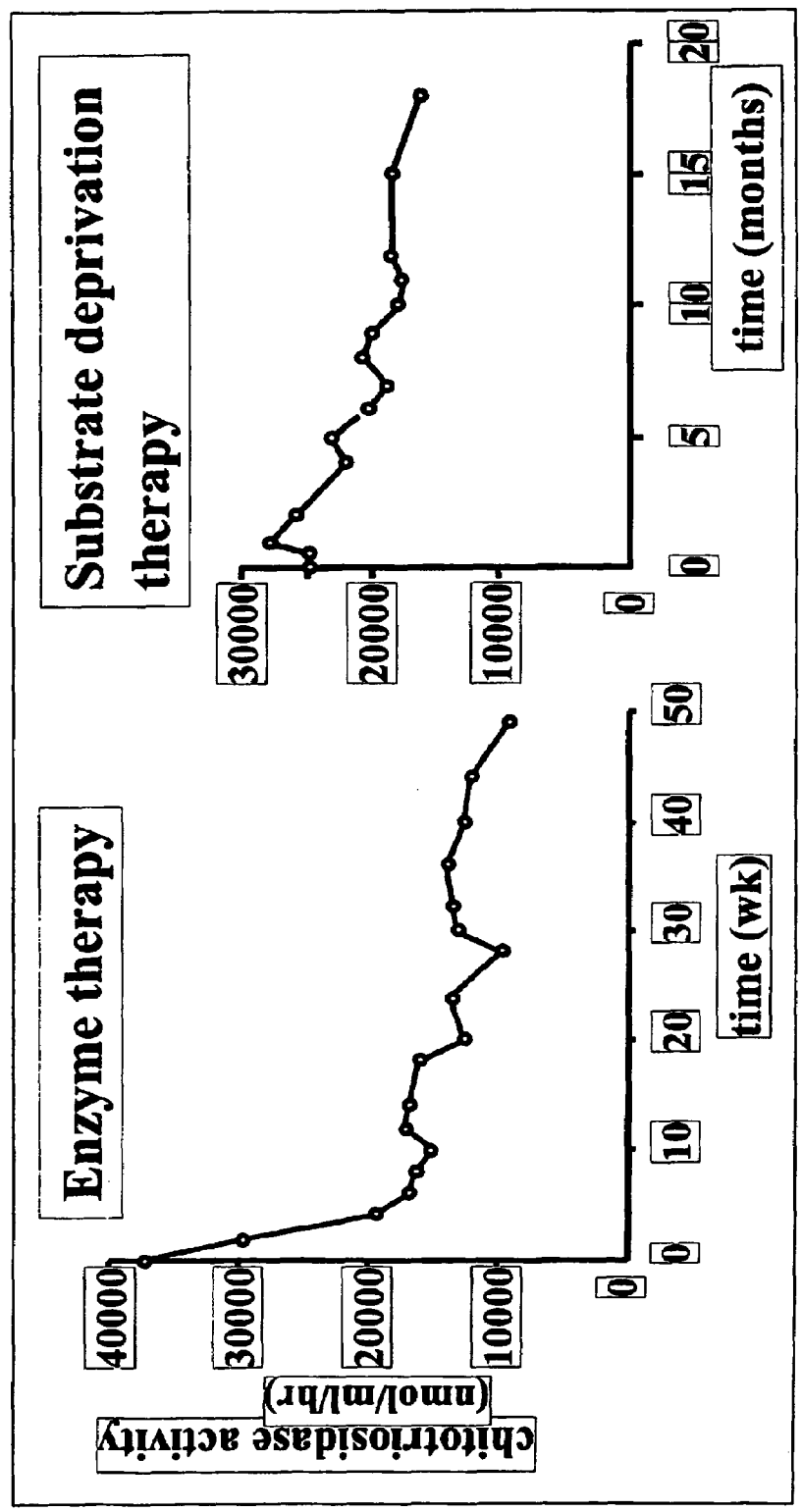
FIG. 7. Corrections in plasma chitotriosidase following therapeutic interventions. Responses in plasma enzyme level in the first patient in Europe treated with enzyme replacement therapy (aiglucerase) and the first patient in Europe treated with substrate deprivation therapy (butyldeoxynojirimycin). Enzyme activities were measured with 4MU-chitotriose as described in Hollak et al., 1994.
Figure 8:
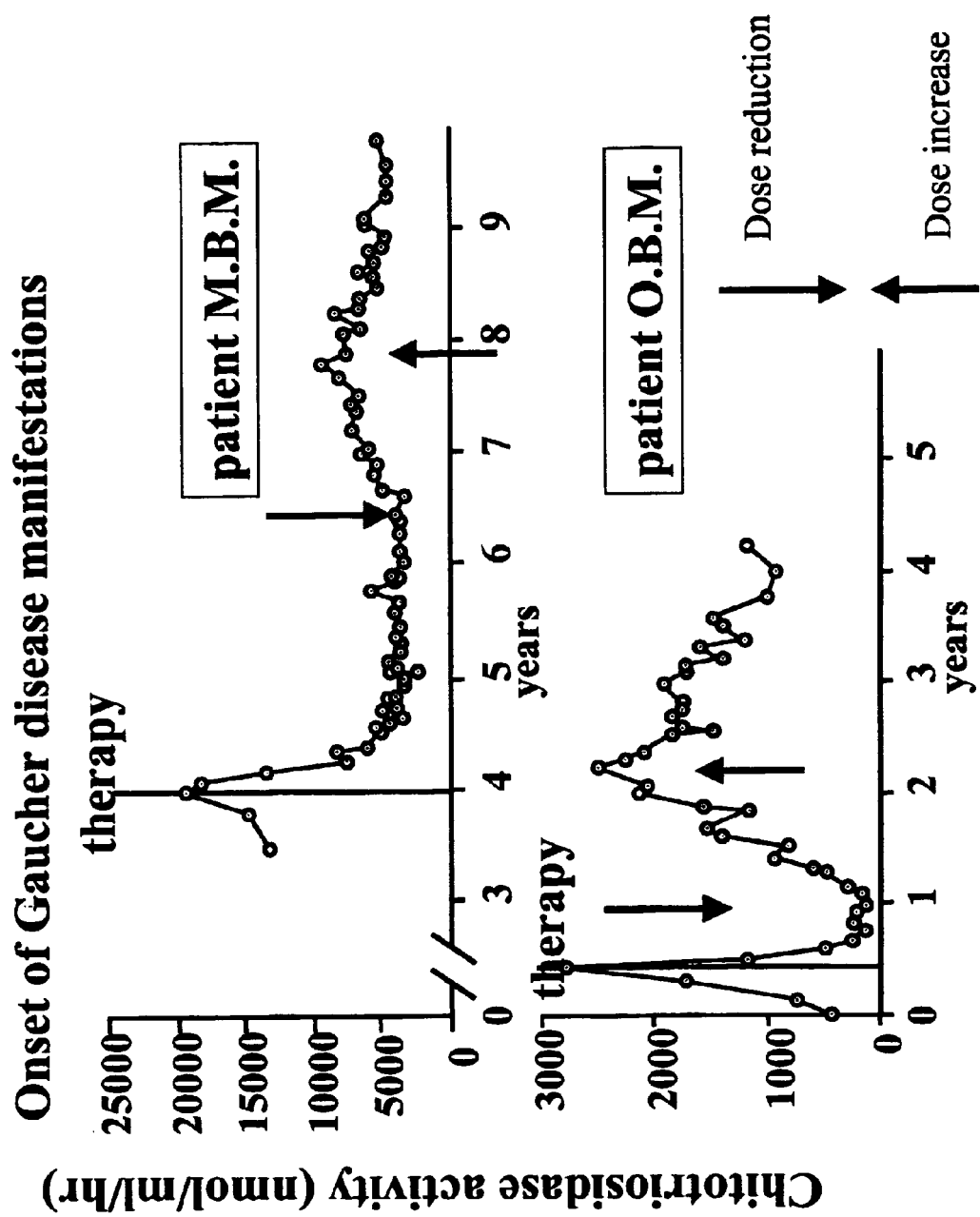
FIG. 8. Monitoring of plasma chitotriosidase during onset and therapy of Gaucher patients. Changes in plasma chitotriosidase in two sisters (L444P glucocerebrosidase homozygotes) suffering from type III Gaucher disease. Enzyme activity increases during onset of disease and is corrected following enzyme replacement therapy. Reductions in aiglucerase dose were accompanied by a relapse in chitotriosidase level and clinical complications. Plasma chitotriosidase levels were measured using the method described in Hollak et al., 1994.
Figure 9:
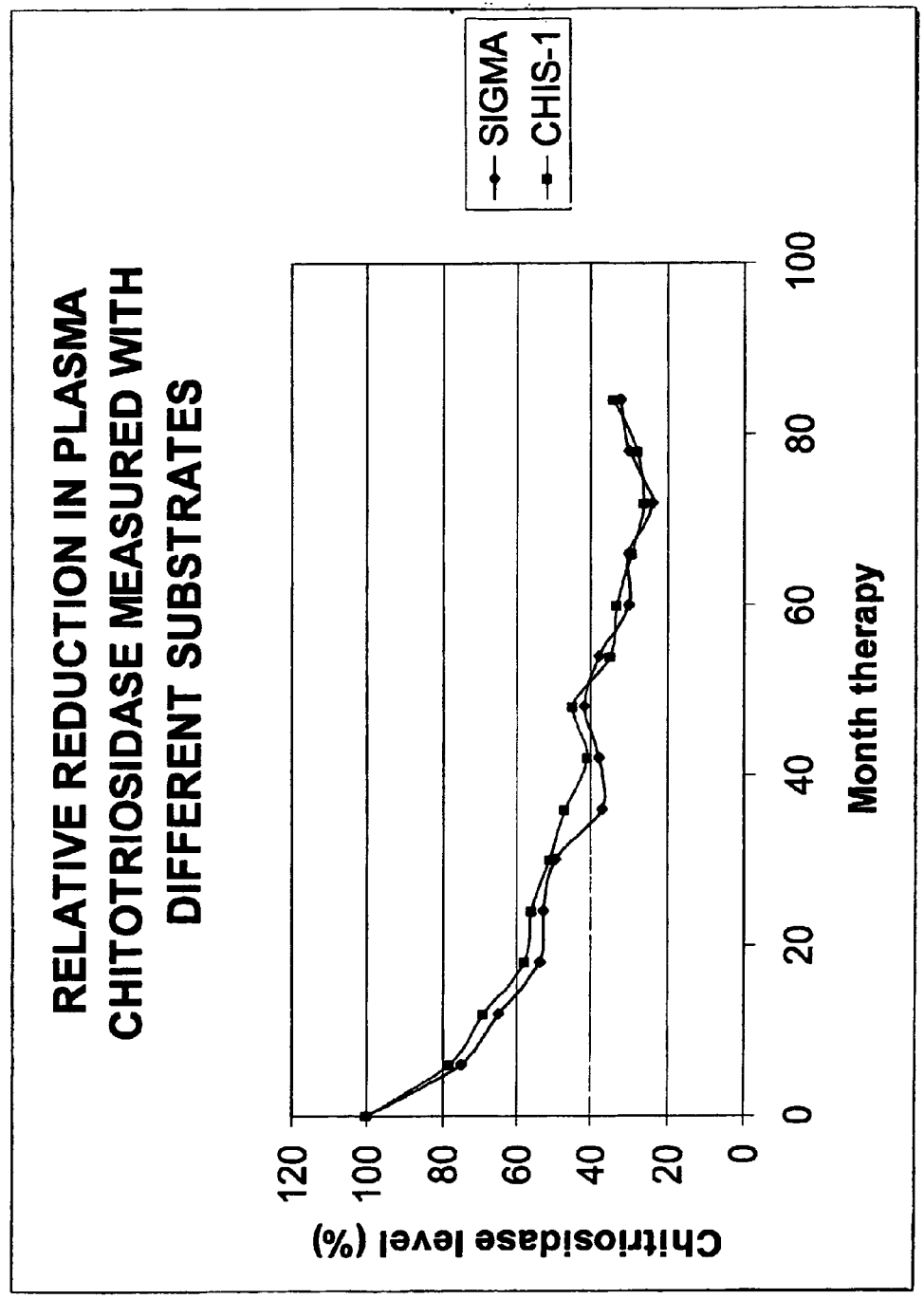
FIG. 9. Example of correction in plasma chitotriosidase in type 1 Gaucher patient following successful enzyme therapy. Comparison of old and novel activity measurement. Plasma chitotriosidase levels were measured with 4MU-chitotriose (Sigma) using the method described in (Hollak et al., 1994) or with 150 microM CHIT-i at the same conditions.
Figure 10:
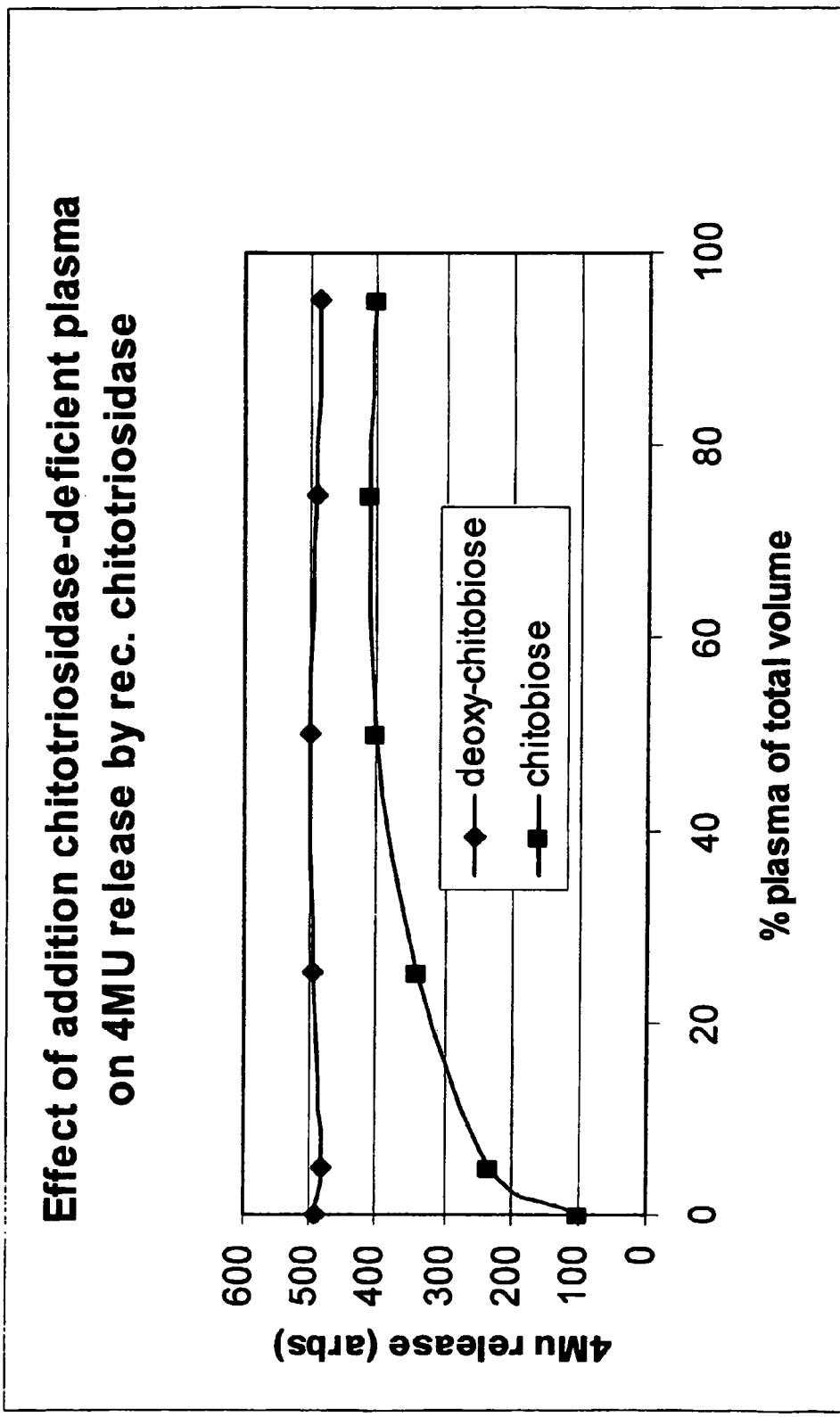
FIG. 10. Presence of acceptor in human plasma that allows stimulation of enzyme assay. Recombinant 50 kDa chitotriosidase was measured with CHIS-1 or 4MU-chitobiose in the presence of increasing amounts of plasma (assay volume %) obtained from a chitotriosidase-deficient donor.

By spiking plasma samples with pure chitotriosidase the CHIS-kit was validated. FIG. 5 shows that the method allows a very reliable, convenient detection of chitotriosidase levels in plasma/serum samples. The presence of lysozyme or other chitinolytic enzymes no longer interferes with the results and chitotriosidase deficiency can be accurately detected.

Example IV

Synthesis of 4-methylumbellyferyl 2-acetamido-2-deoxy-4-0-(2-acetamido-2,4-dideoxy-beta-D-glucopyranosyl)-beta-Dglucopyranoside (CHIS-1; (4-deoxy-GlcNAc)-GlcNAc-UMB). Chitin was purchased from Sigma. 1-(Benzoyloxy)benzotriazole was prepared according to the literature procedure (Kim et al., 1985). All other reagents were purchased either from Aldrich or Baker.

Octaacetylchitobiose, prepared by acetolysis of chitin (Inaba et al., 1984), was transformed into 2-acetamido-1,3,6-tri-O-acetyl-2-deoxy-4-O-(2-acetamido-3-0-acetyl-2- deoxy-beta-D-glucopyranosyl)-beta-D-glucopyranose following the literature procedure (Shaban et al, 1971). Regioselective benzoylation of the 6'-OH group by treatment with 1-(benzoyloxy)benzotriazole followed by a Barton deoxygenation procedure (Barton et al., 1975) (treatment with 1,1'-thiocarbonyldiimidazole and then tri-n-butytin hydride in the presence of azoisobutyronitrile) afforded the corresponding 4'-deoxy chitobiose derivative. Subsequent chlorination, condensation with the sodium salt of 4-methylumbelliferone, as described in the literature (Delmotte et al., 1975), and final de-O-acylation under basic conditions furnished the target compound (4-deoxy-GlcNAc)-GlcNAc-UMB, the structure of which is depicted in FIG. 11.

Example V

Substrate preference of lysozyme. The enzymatic activity of commercial lysozyme preparations was 25 measured with 4-MU-chitobioside and 4MU-deoxychitbioside substrates. The release of 4MU was detected fluorimetrically, as described before. Similar to the findings for chitotriosidase (chitinase), the activity measured with the deoxy-subsytrate is far higher:

| Enzyme preparation (obtained from Sigma) | ratio 4MU-deoxychitobioside/ 4Mu-chitobioside |
| --- | --- |
| lysozyme from human milk | 2.5-3.0 |
| lysozyme from chicken egg | 2.1-2.4 |
| lysozyme from human neutrophils | 3.0-3.2 |

It is concluded that also for lysozyme activity measurements the novel substrate is also superior to the conventional substrate.

REFERENCES

Aerts J. M. F. G., Hollak C. E. M. (1997): Plasma and metabolic abnormalities in Gaucher disease. Bailliere Clin.Hematol.1O, 691-709

Barone R., Di Gregorio F, Romeo M. A., Schiliro G, Pavone L. (1999): Plasma chitotriosidase activity in patients with beta-thalassemia. Blood Cells Mol.Dis. 25,1-8

Bame K. (2001): Heparanase: endoglycosidases that degrade heparan sulfate proteoglycans. Mini review. Glycobiology 11 (6): 91R-98R Barton, D. H. R., and McCombie, S. W. (1975). J. Chem. Soc., Perkin Trans. I, 1574-1585.

Beguin P., Aubert J. P. (1994): The biological degradation of cellulose. FEMS Microbiol Rev. 13 (1): 25-58

Bladjberg E. M., Larsen L. F., Ostergaard P., Jespersen J. (200): In vitro effects of heparin and tissue factor pathway inhibitor on factor VII assays, possible implications for measurements in vivo after heparin therapy. Blood Coag Fibrinolysis 11 (8): 739-745

Boot R. G., Renkemna G. H., Strijiand A., van Zonneveld A. J., Muysers A. J., Aerts J. M. F. G. (1995): Cloning of cDNA encoding chitotriosidase, a human chitinase produced by macrophages. J. Biol.Chem.270, 26252-26256

Boot R. G., Renkema G. H., Verhoek M., Strijiand A., Bliek J., de Meulemeester T. M. A. M. O., Mannens M. M. A. M., Aerts J. M. F. G. (1998): The human chitotriosidase gene. Nature of inherited enzyme deficiency. J.Biol.Chem.273, 25680-25685

Boot R. G., Achterberg T. A. E., van Aken B. E., Renkema G. H., Jacobs M. H. J. M., Aerts, J. M. F. G., de Vries C. J. M. (1999): Strong induction of members of the chitinase family of proteins in artherosciorosis: chitotriosidase and human cartilage gp-39 expressed in lesion macrophages. Artrioscl.Thromb.Vasc.Biol. 19, 687-694

Boot R. G., Blommaart E. F., Swart E., Ghauharalli-van der\Tlugt K., Biji N., Moe C., Place A., Aerts J. M. F. G. (2001): Identification of a novel acidic mammalian chitinase distinct from chitotriosidase. J. Biol. Chem.276, 6770-6778

Brenchley P. E. C. (2000): Heparanase assay. Patent publication W00077241A2,21 December 2000

Brown F. M. (2000): Urine cytology: It is still the gold standard for screening? Urol Clin North Am. 27 (1): 25-37

Casal J. A., Lacerda L., Perez L. F., Pinto R., Sa Miranda M., Carlos Tutor J. (2002): Relationships between serum markers of monocyte/macrophage activation in type 1 Gaucher disease. Clin.Chem.Lab.Med. 40,52-55

Chamoles N. A., Blanco M., Gaggioli D., Casentini C. (2002): Gaucher and Nieman-Pick diseases—enzymatic diagnosis in dried blood spots on filter paper: retrospective diagnosis in newborn-screening cards. Clin Chim Acta 317, 191-197

Choi E. H. Zimmerman P. A. Foster C. B., Zhu S., Kumaraswami V., Nutman T. B., Chanack S. J. (2001): Genetic polymorphisms in molecules of innate immunity and susceptibility to infection with Wucheria bancroffi in South India. Genes Immun.2, 248-253.

Cottaz S., Brasme B., Driguez H. (2000): A fluorescence-quenched chitopentaose for the study of endo-chitinases and chitobiosidases. Eur J Biochem. 267 (17): 5593-5600

Cox T., Lachmann R., Hollak C. E. M., Aerts J. M., van Weely S., Hrebicek M., Platt F., Butters T., Dwek A., Moyses C., Gow I., Elstein D., Zimran A. (2000): Novel oral treatment of Gaucher disease with N-butyldeoxynojirimycin (OGT 918) to decrease substrate biosynthesis.

Cramer J. A., Bailey L. C., Bailey C. A., Miller R. T. (1994): Kinetic and mechanistic studies with bovine testicular hyaluronidase. Biochim Biophys Acta 18; 1200 (3): 315-321

Delmotte, F. M., Privat, J.-P. D. J., and Monsigny, M. L. (1975). Carbohydr. Res. 40, 353-364.

Desoize B., Jardillier J. (2000): Multicellular resistance: a paradigm for clinical resistance? Crit Rev Oncol Hematol. 36 (2-3): 193-207

Freeman C. G., Parish C. R. (2001): Detection of mammalian heparanase activity and purification of mammalian heparanase. U.S. Pat. No. 6,207,402 Bi Frost G. I., Stem R. (1997): A microtiter-based assay for hyaluronidase activity not requiring specialized reagents. Anal Biochem 5; 251 (2): 263-269

Giraldo P., Cenarro A, Alfonso P., Perez-Calvo J. I., Rubio-Felix D., Giralt M., Pocovi M. (2002) Chitotriosidase genotype and plasma activity in patients with type 1 Gaucher disease and their relatives (carriers and non carriers). Hematologica 86,977-984

Guo Y., He W., Boer A. M., Wevers R. A., de Bruijn A. M., Groener J. E. M., Hollak C. E. M., Aerts J. M. F. G., van Diggelen O. P. (1995): Elevated plasma chitotriosidase in various lysosomal disorders. J.Inher.Met.Dis. 18, 717-722

Hollak C. E. M., van Weely S., van Oers M. H. J., Aerts H. M. F. G. (1994): Marked elevation of plasma chitotriosidase activity. A novel hallmark of Gaucher disease. J Clin Invest. 93: 1288-1292

Inaba, T., Ohgushi, T., Iga, T., and Hasegawa, E. (1984) Chem. Pharm. Bull. 32, 1597-1603.

Kim, S., Chang, H., and Kim, W. J. (1985) J. Org. Chem. 50, 1751-1752

Labadaridis J., Dimitriou E., Aerts J. M., van Weely S., Donker-Koopman W., Michelakakis H. (1998): Serial chitotriosidase activity estimations in neonatal systemic candidiasis. Acta.Paed. 87,605

Lauw F. N., TeVelde A. A., Dekkers P. E. P., Speelman P., Aerts J. M. F. G., Hack C. E., van Deventer S. J. H., van der Poll T. (1999): Activation of mononuclear cells by interleukin-12: an in vivo study in chimpanzees. J.Clin.Immunol. 19,231-238.

Lin G., Stern R. (2001): Plasma hyaluronidase (Hyal-1) promotes tumour cell cycling. Cancer Letters 10; 163 (1): 95-101

Lokeshwar V. B., Block N. L. (2000): HA-HAase urine test. A sensitive and specific method for detecting bladder cancer and evaluating its grade. Urol Clin North Am. 27 (1): 53-61

Maeda K., Ito K., Yamaguchi N. (1980): A simple lysoplate method of lysozyme determination with samples dried on filter paper. Clin Chim Acta 15; 100 (2): 175-181

McKenzie E., Tyson K., Stamps A., Smith P., Turner P., Barry R., Hircock M., Patel S., Barry E., Stubberfield C., Terret J., Page M. (2000): Cloning and expression profiling of Hpa2, a novel mammalian heparanase family member. Biochem Biophys Res Commun. 276 (3): 1170-1177

Menzel E. J., Farr C. (1998): Hyaluronidase and its substrate hyaluronan: biochemistry, biological activities and therapeutic uses. Cancer Letters 131: 3-11

Miura R. O., Yamagata S., Miura Y., Harada T., Yamagata T. (1995): Analysis of glycosaminoglycan-degrading enzymes by substrate gel electrophoresis (zymography). Anal Biochem. 1; 225 (2): 333-340

Morsky P. (1983): Turbidimetric determination of lysozyme with Micrococcus lysodeikticus cells: Reexamination of reaction conditions. Anal Biochem. 128: 77-85

Muckenschnabel I., Bernhardt G., Spruss T., Dieti B., Buschauer A. (1998): Quantitation of hyaluronidases by the Morgan-Elson reaction: comparison of the enzyme activities in the plasma of tumour patients and healthy volunteers. Cancer Letters 131: 13-20

Parish C. R., Freeman C., Brown K. J., Francis D. J., Cowden W. B. (1999): Identification of sulphated oligosaccharide-based inhibitors of tumour growth and metastasis using novel in vitro assays for angiogenesis and heparanase activity. Cancer Res. 59 (14): 3433-3441

Parish C. R., Freeman C., Hulett M. D. (2001): Heparanase: a key enzyme involved in cell invasion. Biochmica et Biophysica Acta 1471: M99-M108

Pattanaargson S., Roboz J. (1996): Determination of hyaluronidase activity in venoms using capillary electrophoresis. Toxicon 34 (10): 1107-1117

Payre N., Cottaz S., Driguez H. (1995): Chemoenzymatic synthesis of a modified pentasaccharide as a specific substrate for a sensitive assay of aamylase by fluorescence quenching. Angew Chem Tnt. 34: 1239-1241

Renkema G. H., Boot R. G., Muysers A. O., Donker-Koopman W., Aerts J. M. F. G. (1995): Purification and characterization of human chitotriosidase, a novel member of the chitinase family of proteins. J.Biol.Chem.270, 2198-2202

Renkema G. H., Boot R. G., Strijiand A., Donker.Koopman W., van den Berg M., Muysers A. O., Aerts J. M. F. G. (1997): Synthesis, sorting and processing into distinct isoforms of human macrophage chitotriosidase. Eur.J.Biochem. 244,279-285.

Renkema G. H., Boot R. G., Fung L. A., Donker-Koopman W., Strijiand A., Muysers A. O., Hrebicek M., Aerts J. M. F. G. (1998): Chitotriosidase, a chitinase and human cartilage glycoprotein of 39 kDa, a chitin-binding lectin, are homologues of the family 18 of glucosyihydrolases secreted bu human macrophages. Eur.J.Biochem. 251, 504-509

Shaban, M., and Jeanloz, R. W. (1971): The synthesis of 2.acetamido-2-deoxy-4-0-L-fucopyranosyl-D-glucose. Carbohydr. Res. 19, 311-318.

Spindler K.-D, (1997): Chitinase and chitosanase assays. In Chitin Handbook (Muzzarelli, R. A. A. & Peters, M. G., eds): 229-235. European Chitin Society, Atec Edizioni, Grottammare, Italy Takagaki K., Nakamura T., Izumi J., Saitoh H., Endo M., Kojima K., Kato I., Majima M. (1994): Characterization of hydrolysis and transglycosylation by testicular hyaluronidase using ion-spray mass spectrometry. Biochemistry 31; 33 (21): 6503-6507

Tambe A. S., Kaore S. B., Sawane M. V., Gosavi G. B. (2001): Acrosome intactness and seminal hyaluronidase activity: relationship with conventional seminal parameters. Indian J Med Sci. 55 (3): 125-132

Taylor D. C., Cripps A. W., Clancy R. L. (1992): Measurement of lysozyme by an enzyme-linked immunosorbent assay. J Immunol Methods 146 (1): 55-61

Vlodavsky I., Friedmann Y. (2001): Molecular properties and involvement of heparanase in cancer metastasis and angiogenesis. J Clin Invest. 108 (3): 341-347

Vom Dahl S., Harzer K., Rolfs B., Albrecht B., Niederau C., Vogt C., van Weely S., Aerts, J. M., Muller G., Haussinger D. (1999): Hepatosplenomegalic lipidosis: what unless Gaucher? Adult cholestryl storage disease (CESD) with anemia, mesenteric lipodystrophy, increased chitotriosidase activity and a homozygous acid lipase-exon 8 splice junction mutation. J.Hepatol.31, 741-746.

Young E., Chatterton C, Vellodi A., Winchester B.(1997): Plasma chitotriosidase activity in Gaucher disease patients who have been treated either by bone marrow transplantation or by enzyme replacement therapy with alglucerase. J. Inherit. Met. Dis. 20, 595-562.

What is claimed is:

1. A method for detecting the activity of a human chitinase, the method comprising:
   (i) combining a human chitinase with a modified substrate that comprises both a detectable leaving group and an oligosaccharide modified by substituting a hydrogen atom or a methoxy group for a hydroxyl group at the C4 position of the non-reducing end of a N-acetylglucosamine moiety of said oligosaccharide; and
   (ii) detecting cleavage of the substrate by measuring release of the detectable leaving group;
   wherein said modification of the chitinase substrate permits its cleavage by the chitinase and inhibits the transglycosidase activity of the chitinase.

2. The method according to claim 1, wherein the transglycosidase activity is inhibited upon the combination of another oligosaccharide acceptor capable of being glycosylated by the human chitinase in the presence of said modified substrate.

3. The method according to claim 2, wherein the other oligosaccharide acceptor capable of being glycosylated by the human chitinase is of serum origin.

4. The method according to claim 2, wherein the other oligosaccharide acceptor consists of 2 -5 sugar moieties.

5. The method according to claim 1, wherein the detectable leaving group comprises 4-methyl-umbelliferyl, para-nitrophenyl, or fluorescein capable of being detected after being cleaved from the modified substrate.

6. The method according to claim 1, wherein the modified substrate for the human chitinase is 4-methylumbelliferyl-(4-deoxy)-chitobiose.

7. The method according to claim 1, wherein the human chitinase is a chitotriosidase.

8. The method according to claim 1, further comprising: comparing the activity of the human chitinase with a reference value.

9. The method according to claim 1, further comprising: at least partially isolating the human chitinase from a sample before combining the modified substrate with the human chitinase.

10. The method according to claim 9, wherein isolating the human chitinase comprises binding the human chitinase with an antibody capable of specifically binding the human chitinase.

11. A method for detecting the activity of a human chitinase in a biological sample, the method comprising:
   (i) isolating a biological sample comprising a human chitinase;
   (ii) combining the sample with a modified substrate capable of generating a detectable signal upon cleavage by a human chitinase, wherein the modified substrate comprises a detectable leaving group and an oligosaccharide modified by substituting either a hydrogen atom or a methoxy group for a hydroxyl group at the C4 position of the non-reducing end of a N-acetylglucosamine moiety of said oligosaccharide; and
   (iii) measuring the detectable signal generated by release of the detectable leaving group
   wherein said modification of the chitinase substrate permits its cleavage by the chitinase and inhibits the transglycosidase activity of the chitinase.

12. The method according to claim 11, wherein the sample is a blood sample.

13. The method according to claim 11, wherein the detectable signal comprises the formation of a fluorescent compound upon cleavage by the human chitinase.

14. The method of claim 13 wherein the detectable leaving group comprises 4-methyl-umbelliferyl, para-nitrophenyl, or fluorescein.

15. The method according to claim 11, further comprising isolating the human chitinase by contacting the sample with an antibody capable of binding the human chitinase.

* * * * *

UNITED STATES PATENT AND TRADEMARK OFFICE
CERTIFICATE OF CORRECTION

| | | |
|---|---|---|
| PATENT NO. | : 7,632,654 B2 | Page 1 of 1 |
| APPLICATION NO. | : 10/977509 | |
| DATED | : December 15, 2009 | |
| INVENTOR(S) | : Johannes Maria Franciscus Gerardus Aerts | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 65 days.

Signed and Sealed this

Second Day of November, 2010

David J. Kappos
*Director of the United States Patent and Trademark Office*